US006180355B1

(12) United States Patent
Alexander et al.

(10) Patent No.: US 6,180,355 B1
(45) Date of Patent: Jan. 30, 2001

(54) METHOD FOR DIAGNOSING AND TREATING CHRONIC PELVIC PAIN SYNDROME

(75) Inventors: Richard B. Alexander; Sathibalan Ponniah, both of Ellicott City, MD (US)

(73) Assignee: University of Maryland, Baltimore, Baltimore, MD (US)

( * ) Notice: Under 35 U.S.C. 154(b), the term of this patent shall be extended for 0 days.

(21) Appl. No.: 09/306,927

(22) Filed: May 7, 1999

Related U.S. Application Data

(60) Provisional application No. 60/084,668, filed on May 7, 1998.

(51) Int. Cl.[7] ............................. G01N 33/50; G01N 33/53

(52) U.S. Cl. ............................................. 435/7.1; 435/7.8

(58) Field of Search .......................... 435/7.1, 7.8, 7.92, 435/7.94; 424/1.41, 145.1, 158.1; 436/501, 86, 87

(56) References Cited

PUBLICATIONS

Yasumoto et al. (1995) Seminal plasma cytokines in non-bacterial prostatitis: Changes following sparfloxacin treatment. Acta Urologica Japonica 41: 771–774. (English abstract only, BIOSIS accession No. 1996: 70462).*
Depuydt et al. (1996) The relation between reactive oxygen species and cytokines in andrological patients with or without male accessory gland infection. J. Andrology, 17: 699–707.*
Naz et al. (1994) Increased levels of interleukin–6 in seminal plasma of infertile men. J. Andrology 15: 220–227.*
R.B. Alexander, F. Brady and S. Ponnian, "Autoimmune Prostatitis: Evidence of T Cell Reactivity with Normal Prostatic Proteins," Urology, 50(6) pp. 893–899. 1997.

Ryoji Yasumoto et al., "Seminal Plasma Cytokines in Non-bacterial Prostatitis: Changes Following Sparfloxacin Treatment," Acta Urol. Jpn., 1995, 41: pp.771–774.

F. Comhaire et al., "Cytokines in Semen of Normal Men and of Patients With Andrological Diseases," American Journal of Reproductive Immunology, 1994, 1994, 31: pp. 99–103.

Kouichiro Shimoya et al., "Detection of Monocyte Chemotactic and Activating Factor (MCAF) and Interleukin (IL)–6 in Human Seminal Plasma and Effect of Leukospermia on These Cytokine Levels," American Journal of Reproductive Immunology, 1995, 34: pp. 311–316.

Taiji Nishimura et al., IL–1ra Versus IL–1 Levels in Prostatic Fluid from Prostatitis Patients, Urol Int 1998, 60: pp. 92–96.

Taiji Nishimura et al., "Low Levels of IL–1ra Versus IL–1 Levels in Prostatic Fluid Are Not a Cause of Prolongation of Prostatitis," J. Nippon Med. Sch., 1996, 63 (6): pp. 62–63.

Maryann Nocera and T. Ming Chu, "Characterization of Latent Transforming Growth Factor–β From Human Seminal Plasma," American Journal of Reproductive Immunology, 1995, 33: pp. 282–291.

(List continued on next page.)

Primary Examiner—Robert A. Schwartzman
Assistant Examiner—Thomas G. Larson
(74) Attorney, Agent, or Firm—Steven J. Hultquist; William A. Barrett

(57) ABSTRACT

The present invention provides a superior method of diagnosing Chronic Pelvic Pain Syndrome in men comprising measuring levels of cytokines in semen or components or fractions of semen. The invention also provides a method of treating a condition associated with elevated levels of a cytokine, such as TNF-α, in semen or a component or fraction thereof, comprising administering a therapeutically effective amount of an ant-cytokine compound or composition, such as an anti-TNF-α compound or composition.

14 Claims, 8 Drawing Sheets

PUBLICATIONS

Maryann Nocera and T. Ming Chu, "Transforming Growth Factor β as an Immunosuppressive Protein in Human Seminal Plasma," American Journal of Reproductive Immunology, 1993, 30: pp. 1–8.

Bernadette Loras et al., "Seminal Transforming Growth Factor–β in Normal and Infertile Men," Human Reproduction, 1999, 14 (6): pp. 1534–1539.

Fiona C. Denison et al., "Seminal Plasma Components Stimulate Interleukin–8 and Interleukin–10 Release," Molecular Human Reproduction, 1999, 5 (3):pp.220–226.

E. Koumantakis et al., "Increased Levels of Interleukin–8 in Human Seminal Plasma," Andrologia, 1998, 30: pp. 339–343.

G. Frenette et al., "High Concentrations of the Macrophage Migration Inhibitory Factor in Human Seminal Plasma and Prostatic Tissues," Archives of Andrology, 1998, 41: pp. 185–193.

Alexander E. Omu et al., "Antibiotic Therapy of Seminal Infection Effect on Antioxidant Activity and T–Helper Cytokines," The Journal of Reproductive Medicine, 1998, 43 (10): pp. 857–864.

I. Matalliotakis et al., "Cytokine Levels in Seminal Plama," Clin. Exp. Obst. & Gyn., 1998, 25 (1–2): pp. 58–60.

I. Matalliotakis et al., "Interleukin–6 in Seminal Plasma of Fertile and Infertile Men," Archives of Andrology, 1998, 41: pp. 43–50.

Rajesh K. Naz and Lori Evans, "Presence and Modulation of Interleukin–12 in Seminal Plasma of Fertile and Infertile Men," Journal of Andrology, 1998, 19 (3): pp. 302–307.

M. Fujisawa et al., "Levels of Interferon α and γ in Seminal Plasma of Normozoospermic, Oligozoospermic, and Azoospermic Men," Archives of Andrology, 1998, 40: pp. 211–214.

D.J. Anderson et al., "Quantitation of Mediators of Inflammation and Immunity in Genital Tract Secretions and Their Relevance to HIV Type 1 Transmission," AIDS Research and Human Retroviruses, 1998, 14 (Supplement 1): pp. S43–S49.

Roberto Paradisi et al., "T–Helper 2 Type Cytokine and Soluble Interleukin–2 Receptor Levels in Seminal Plasma of Infertile Men," American Journal of Reproductive Immunology, 1997, 38: pp. 94–99.

Brigitte Dousset et al., "Seminal Cytokine Concentrations (IL–1β, IL–2, IL–6, sR IL–2, sR IL–6), Semen Parameters and Blood Hormonal Status in Male Infertility," Human Reproduction, 1997, 12 (7): pp. 1476–1479.

Mahmoud Huleihel et al., "Distinct Expression of Cytokines and Mitogenic Inhibitory Factors in Semen of Fertile and Infertile Men," American Journal of Immunology, 1997, 37: pp. 304–309.

Matthias S. Gruschwitz et al., "Cytokine Levels in the Seminal Plasma of Infertile Males," Journal of Andrology, Mar./Apr. 1996, 17 (2): pp. 158–163.

Lawrence F. Brown et al., "Vascular Permeability Factor (Vascular Endothelial Growth Factor) Is Strongly Expressed in the Normal Male Genital Tract and is Present in Substantial Quantities in Semen," The Journal of Urology, Aug. 1995, 154: pp. 576–579.

R. Paradisi et al., "Interleukin–2 in Seminal Plasma of Fertile and Infertile Men," Archives of Andrology, 1995, 35: pp. 35–41.

Mahadevan Rajasekaran et al., "Oxidative Stress and Interleukins in Seminal Plasma During Leukocytospermia," Fertility and Sterility, Jul. 1995, 64 (1): pp. 166–171.

Rajesh K. Naz and Paul Kaplan, "Increased Levels of Interleukin–6 in Seminal Plasma of Infertile Men," Journal of Andrology, May/Jun. 1994, 15 (3): pp. 220–227.

S. Shimonovitz et al., "High Concentration of Soluble Interleukin–2 Receptors in Ejaculate with Low Sperm Motility," Human Reproduction, 1994, 9 (4): pp. 653–655.

Nina–Beate Liabakk et al., "High Concentrations of the Soluble p55 Tumour Necrosis Factor Receptor in Human Seminal Plasma," Human Reproduction, 1993, 8 (11): pp. 1837–1842.

Y. Hirata et al., "Epidermal Growth Factor in Human Seminal Plasma," Horm. Metabol. Res., 1987, 19: pp. 35–37.

Roger D. Kempers, "Distinct Expression Levels of Cytokines and Soluble Cytokine Receptors in Seminal Plasma of Fertile and Infertile Men," Fertility and Sterility, Jul. 1996, 66(1): pp. 135–139.

* cited by examiner

| APC PULSED WITH: | PROSTATITIS PATIENTS | p¹ (VS UNPULSED) | NORMAL DONORS | p¹ (VS UNPULSED) |
|---|---|---|---|---|
| UNPULSED | 1,602(597) | | 953(359) | |
| TETANUS | 18,059(5045) | 0.002 | 13,196(4,929) | 0.0008 |
| CANDIDA | 16,955(4296) | 0.015 | 11,783(2,657) | 0.0007 |
| SEMINAL PLASMA | 13,365(6,027) | 0.001 | 1,321(311) | 0.21 |

WILCOXON SIGNED-RANK TEST, p. VALUE 2-TAILED.

FIG.2

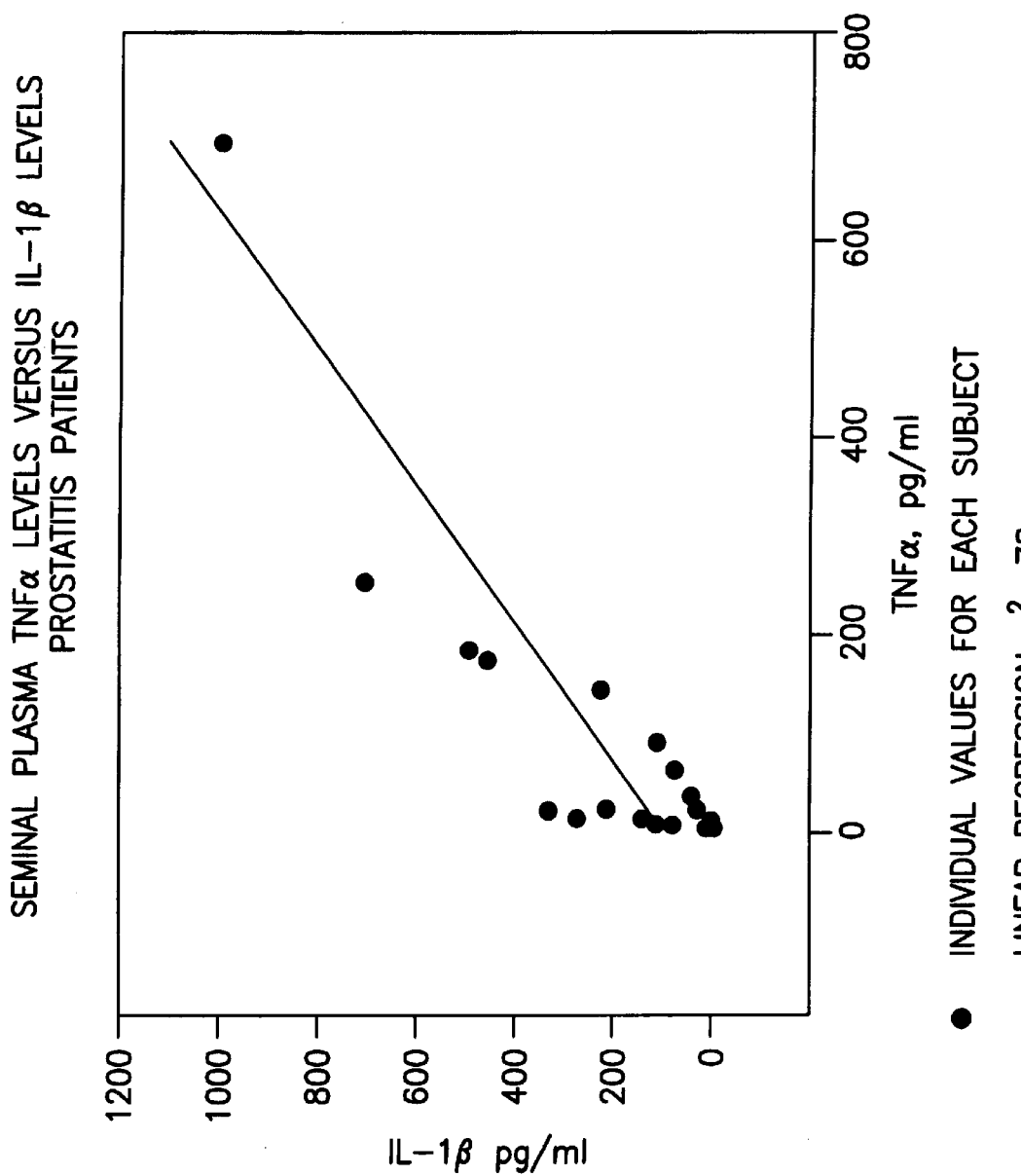

METHOD FOR DIAGNOSING AND TREATING CHRONIC PELVIC PAIN SYNDROME

CROSS-REFERENCE TO RELATED APPLICATION

This application claims benefit of U.S. Provisional Application No. 60/084,668, filed on May 7,1998.

BACKGROUND OF THE INVENTION

Chronic prostatitis/chronic pelvic pain syndrome (collectively referred to herein as CPPS) is a syndrome of undetermined etiology occurring in men. CPPS is the third of four subgroups of prostatitis recognized by the NIH. Category I encompasses acute bacterial prostatitis, and Category II covers chronic bacterial infection. Category III, CPPS, includes all remaining prostatitis syndromes, and is subdivided into IIIa (inflammatory) and IIIb (non-inflammatory). These sub-categories can be distinguished by the presence of leukocytosis in expressed prostatic secretions or sediment in a post-massage urine sample. Finally, Category IV represents asymptomatic prostatitis, which often is associated with benign prostate hyperplasia.

Prostatitis is extraordinarily common, resulting in approximately 2 million office visits to primary care physicians and urologists in the United States annually [1997 American Urological Association Annual Meeting, National Ambulatory Medical Care Survey, National Center for Health Statistics, 1990 to 1994]. Patients with CPPS suffer from chronic, episodic pain in the perineum or pelvic region, irritative and obstructive voiding symptoms, and adverse effects upon sexual function [Alexander et al., *Urology* 48:568–574 (1996)]. Men with chronic prostatitis often require repeated physician visits, commonly to different physicians. Medical expenditures relating to CPPD are conservatively estimated to exceed half a billion dollars annually.

Bacterial vs. Non-Bacterial Prostatitis

Given its apparent prevalence, CPPS has defied characterization to an almost astonishing extent. While an enormous number of patients seek the care of a physician because of prostatitis-like symptoms, almost nothing is known about diagnostic criteria, etiology, or objective signs for CPPS. In a survey conducted through the Internet of 163 men with a diagnosis of prostatitis, Alexander and Trissel found that pain in the pelvic region was the most frequently reported and the most severe symptom in such patients [Alexander et al., *Urology* 48:568–74 (1996)]. It was because of these observations and the paucity of objective criteria for defining the disease, that the National Institute of Diabetes and Digestive and Kidney Diseases working group in prostatitis suggested that the disease be named Chronic Pelvic Pain Syndrome.

One reason for the present state of confusion regarding CPPS is the similarity of CPPS symptoms to the symptoms of bacterial prostatitis. Only about 5 to 10% of patients whose symptoms are consistent with bacterial prostatitis are shown to have infection in the prostate gland [Weidner et al., *Infection* 19:S109–S190 (1991)]. The misdiagnosis of CPPS as infectious prostatitis, commonly results in unnecessary treatment with multiple courses of antibiotics at enormous cost to patients and to the health care system with no clearly demonstrated benefit to patients.

An enormous amount of effort has attended the search for a fastidious organism as the cause of CPPS. No clear consensus has emerged identifying any such organism as the causative agent. Published studies have proven difficult to interpret due to lack of a standardized definition of CPPS and the variability in methodologies for detecting infectious organisms. Another difficulty with published studies is that the presence of normal flora in the male urethra complicates the interpretation of culture data. Further, many published studies lack control groups to which the findings in men with prostatitis must be compared.

Recently, Krieger et al. reported an extensive study examining trans-perineal prostate biopsies in 135 men with CPPS for bacterial 16s rRNA-encoding DNA sequences [Krieger et al, *J. Clin. Microbiol* 34:3120–3128 (1996)]. Krieger et al. found that 77% of the CPPS patients had bacterial DNA sequences in their prostatic tissue that were distinct from normal bowel and skin flora. Patients with bacterial DNA sequences in the prostate also had higher numbers of leukocytes in the prostatic fluid compared to patients without such DNA sequences. Krieger et al. concluded that bacteria distinct from the normal bowel and skin flora are present in the prostatic tissue of men with CPPS and are therefore a potential causative agent of CPPS.

In another study by the same group, Berger et. al reported that an aerobic or anaerobic bacterial organism could be cultured from the prostate tissue in 32% of 85 symptomatic men by performing cultures of trans-perineal needle biopsies in a specialized microbiology laboratory [Berger et al., *J. Urol.* 157:863–865 (1997)].

However, the Krieger et al. and Berger et al. data cannot be interpreted as positively identifying a causative agent for prostatitis because neither study compared the CPPS group with a control group lacking symptoms of CPPS to demonstrate that the prostate tissue of subjects without CPPS symptoms does not contain such bacterial DNA sequences. Furthermore, in preliminary data, the present inventors have detected similar diverse bacterial 16s rRNA-encoding DNA sequences in 8/9 patients undergoing transperineal radioactive seed implantation for localized adenocarcinoma of the prostate, all of whom had no antecedent history of CPPS symptoms [S. Keay et al, *Urology* 53: 487–491, 1999]. Thus, while the data of Krieger et. al. show that bacterial DNA sequences exist in the prostate of men with CPPS, the presence of these sequences is not sufficient to demonstrate a bacterial origin for CPPS.

What is clear, however, is that some men with CPPS have evidence of inflammation of the prostate. While the cellular and cytokine mediators involved in the inflammatory process have been increasingly clarified in the immunologic literature, few studies have investigated the immunobiology of the prostate gland to determine whether CPPS might be arise from an auto-immune condition.

Autoimmunity and the Prostate

Many diseases are known to result from autoimmunity. The present inventors have discovered that CPPS has an autoimmune component. The inventors hypothesize that either (1) the autoimmune component of CPPS results from an autoimmune attack upon the prostate, or (2) that a chronic inflammatory process is maintained in CPPS patients as a result of a breakdown of immunoregulatory mechanisms in the immediate environment of the prostate.

There is a substantial body of evidence demonstrating the occurrence of immunological activity within the prostate gland. However, the nature and cause of this activity, and whether it is detrimental to the host, has not been determined. Inflammatory infiltrates in the prostate are very common. In one study of 162 cases of surgically resected prostatic tissue inflammatory infiltrates were found in 98% [Kohnen et al., *J. Urology* 121:755–60 (1979)]. The infiltrating cells consist of monocytes and activated T and B lymphocytes [Theyer et al., *Lab Invest.* 66:96–107 (1992); Steiner et al., *J. Urology* 151:480–84 (1994)].

A rare form of prostatic inflammation, granulomatous prostatitis, has been characterized, although the etiology of the inflammation is also unknown. One of the major theories about this disease, however, is that it represents an immune reaction against self prostatic proteins induced by infection or manipulation of the gland by previous biopsy or surgical procedure [Stillwell et al., *J. Urology* 138:320–23 (1987); Dhundee et al., *Histopathology* 18:435–41 (1991)].

The disease is also observed after instillation of Bacillus Calmette-Guerin (BCG) into the bladder as a treatment for superficial bladder cancer [Bahnson, *J. Urology* 146:1368–69(1991)].

Recent observations about the existence of subsets of CD4$^+$ T cells has yielded fundamental information about immune responses in humans. CD4$^+$ T cells can be separated into subsets based upon the patterns of cytokines they secrete [Mosmann, *Ann NY Acad. Sci.* 664:89–92 (1992)). CD4$^+$ T cells that secrete IFN-γ and IL-2 are called T helper 1 (Th1) cells. Th1 cells mediate cellular immunity, such as delayed hypersensitivity responses. CD4$^+$ T cells that secrete IL-4 and IL-10 are termed T helper 2 (Th2). Th2 cells are associated with antibody production and allergy. Immune responses mediated by Th1 and Th2 cells can be characterized by the local cytokine environment during the developing immune response.

Zisman et al. found IgG anti-PSA antibody titers to be higher in the serum of men with benign prostate hyperplasia (BPH) compared to controls [Zisman et al., *J. Urology* 154:1052–55 (1995)]. However, of 17 men with chronic prostatitis, Zisman et al. found no difference in mean antibody titer as compared to controls. Zisman et al. speculate that an immunologic mechanism may play a role in the symptomatology of BPH. An alternative explanation is that a Th1 type of response may be occurring in patients with chronic prostatitis/chronic pelvic pain syndrome. In this event, no antibody response would be expected. A further understanding of the local cytokine environment in the prostate will be critical to understanding the nature of the inflammatory response that is occurring in order to more clearly understand the disease.

There remains a major need in the art for an objective means for diagnosing CPPS, to identify the cause or causes of the syndrome and for CPPS treatments that can result in an improvement in symptoms in men with the disease.

Cytokines

Cytokines are small to medium-sized proteins or glycoproteins which mediate potent biological effects on most cell types. [See Mire-Sluis, et al., eds. *Cytokines* (1998); also see Thompson, Angus, ed. *The Cytokine Handbook* (1998)] While cytokines were originally identified as key components in inflammatory processes, it is now known that cytokines are involved in many non-inflammatory physiological processes. Cytokines mediate their effects by binding to specific cell surface receptors which are coupled to intracellular signal transduction and second messenger pathways. More than one hundred cytokines have been identified to date. The inventors have identified the following cytokines as having particular importance in the operation of the present invention: IL8, GM-CSF, IL-β and TNF-α.

IL-8 is a member of the chemokine family of cytokines. IL-8 is produced by many cell types. In general, the biological activity of IL-8 results from its ability to activate the CXC chemokine receptors CXCR1 and CXCR2. Among many other functions, IL-8 acts as a neutrophil chemoattractant and activating factor [Matsushima et al., *Cytokine* 1:2–13 (1989); Matsushima et al., *J. Exp. Med.* 167:1883–1893 (1988); Oppenheim et al.,*Annu. Rev. Immunol.* 9:617–648 (1991)]. Synonyms for IL-8 include neutrophil attractant/activating protein (NAP-1), monocyte derived neutrophil activating peptide (MONAP), monocyte derived neutrophil chemotactic factor (MDNCF), neutrophil activating factor (NAF), leukocyte adhesion inhibitor (LAI), Granulocyte chemotactic protein (GCP). IL-8 can be obtained from known commercial sources.

GM-CSF, or granulocytelmacrophage colony stimulating factor, is a survival and growth factor for haematopoietic progenitor cells, a differentiation and activating factor for granulocytic and monocytic cells, and a growth factor for endothelial cells, erythroid cells, megakaryocytes and T cells [Wong et al., *Science* 228:810–815 (1985); Gough et al., *EMBO. J.* 4:645–653 (1985); Clarke et al., *Science* 236: 1229–1237 (1987); Groopman et al., *New Eng. J. Med.* 321, 1449–1459 (1989)]. GM-CSF is also known as CSFa or pluripoietin-a. GM-CSF can be obtained from known commercial sources.

IL-1β has a wide range of biological activities on many different target cell types including B cells, T cells, and monocytes (Dinarello et al., *Adv. Immunol.* 44:153–205 (1989); Fuhlbrigge et al., *In The Year in Immunology 1988: Immunoregulatory Cytokines and Cell Growth*, Vol. 5, Cruse et al., pp.21–37 (1989); di Giovine et al. *lmmunol. Today* 11:13–20 (1990)]. In vivo, IL-1β induces hypotension, fever, weight loss, neutrophilia, and acute phase response. IL-1β can be obtained from known commercial sources.

IL-6 is a multifunctional cytokine secreted by both lymphoid and non-lymphoid cells which regulates B and T cell function, haematopoiesis and acute phase reactions [Hirano, in The Cytokine Handbook, Thomson, ed., *Academic Press*, London, pp. 169–190 (1991); Kishimoto, *Blood* 74:1–10 (1989); Kishimoto, et al., *Science* 258:593–597 (1992)]. Synonyms for IL-6 include interferon-β$_2$, 26-kDa protein, B cell stimulatory factor 2 (BSF-2), hybridoma/plasmacytoma growth factor (HPGF or IL-HP1), hepatocyte stimulating factor (HSF), monocyte granulocyte inducer type 2 (MGI-2), cytotoxic T cell differentiation and thrombopoietin. IL-6 is produced by a large member of cell types, including lymphoid cells (T cells, B cells) and many non-lymphoid cells including macrophages, bone marrow stromal cells, fibroblasts, keratinocytes, mesangium cells, astrocytes and endothelial cells. IL-6 can be obtained from known commercial sources.

TNF-α is a potent paracrine and endocrine mediator of inflammatory and immune functions. It is also known to regulate growth and differentiation of a wide variety of cell types. TNF-α is selectively cytotoxic for many transformed cells, especially in combination with IFN-γ. In vivo, it leads to necrosis of methylcholanthrene-induced murine sarcomas. Many of the actions of TNF-α occur in combination with other cytokines as part of the "cytokine network" [Manogue et al. In The Cytokine Handbook, Thomson ed., *Academic Press*, London, p. 241–256 (1991); Fiers, *FEBS* 285:241–256 (1991); Ruddle, *Curr. Opin. Immunol.* 4: 327–332 (1992)]. TNF-α is expressed as a type 11 membrane protein attached by a signal anchor transmembrane domain in the propeptide and is processed by a matrix metalloproteinase (Gearing et al., *Nature* 338:225–228 (1994). TNF-α can be obtained from known commercial sources.

SUMMARY OF THE INVENTION

The present invention, in one embodiment, provides a superior method of diagnosing CPPS in men. This aspect of the invention is based on the discovery that the seminal plasma levels of certain cytokines are elevated in patients with CPPS. The cytokine measurements may be accomplished by any available method; however, the sandwich ELISA is the most preferred method. Preferred cytokines include GM-CSF, IL-1-β, IL-8, IL-6, and TNF-α. TNF-α is the most preferred cytokine for use in the diagnostic methods according to the present invention.

In another embodiment, the invention provides a method of treating a condition associated with elevated levels of a cytokine, such as TNF-α, in seminal plasma, comprising administering a therapeutically effective amount of an anti-cytokine compound or composition, such as an anti-TNF-α compound or composition.

The present invention also provides a method for treating CPPS comprising administering a therapeutically effective amount of an ant-cytokine compound or composition, such as an anti-TNF-α compound or composition.

Many anti-cytokine agents, such as anti-TNF-α agents, are known in the art. In one aspect of the present invention, the anti-cytokine agent is selected from the group consisting of inhibitors of cytokine synthesis, inhibitors of cytokine processing, and inhibitors of cytokine activity. In another aspect, the anti-cytokine agent is an anti-TNF-α agent selected from the group consisting of inhibitors of TNF-α synthesis, inhibitors of TNF-α processing, and inhibitors of TNF-α activity.

BRIEF DESCRIPTION OF THE DRAWINGS

FIG. 2 shows the mean (SEM) counts per minute of recall proliferation assay data from FIG. 1.

FIG. 8 shows a comparison of seminal plasma TNF-α levels versus IL-1β levels in prostatitis patients.

DETAILED DESCRIPTION OF THE PREFERRED EMBODIMENTS

The present invention provides a method for diagnosing CPPS comprising analyzing a semen component for an elevated level of a cytokine. The semen component is preferably seminal plasma, and the cytokine is preferably selected from the group consisting of GM-CSF, IL-1-β, IL-8, IL-6, and TNF-. More preferably, the cytokine is TNF-α. The present invention also provides a method for treating the CPPS by administering a cytokine inhibitor, such as a TNF-α inhibitor.

The present inventors evaluated a group of men with a history of CPPS for reactivity with normal seminal plasma as compared to a control group. The control group consisted of 15 individuals, including 3 individuals with no history of any urologic problem or symptoms who underwent leukopheresis, and 12 volunteer male blood donors whose buffy coat leukocytes were obtained 24 hours after blood donation. The CPPS group consisted of 10 men who were referred to the VA Maryland Health Care System Urology Section or the University of Maryland Division of Urology with a history of CPPS.

Figure 1:
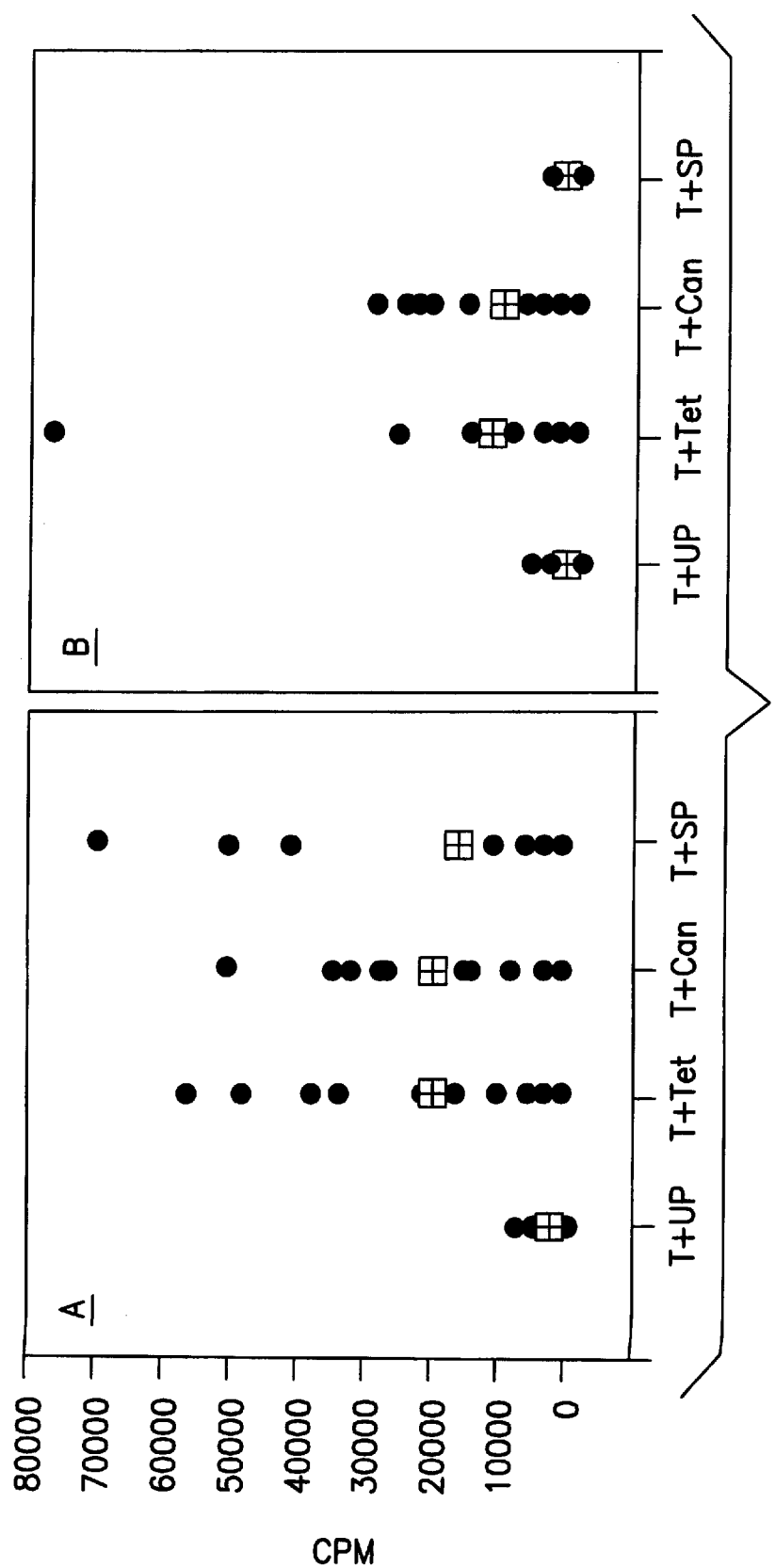
FIGS. 1A and B show the results of recall antigen proliferation assays performed on CD4+ T lymphocytes. The A) panel represents patients with a history of CPPS, and B) panel represents normal patients.
Figure 3:
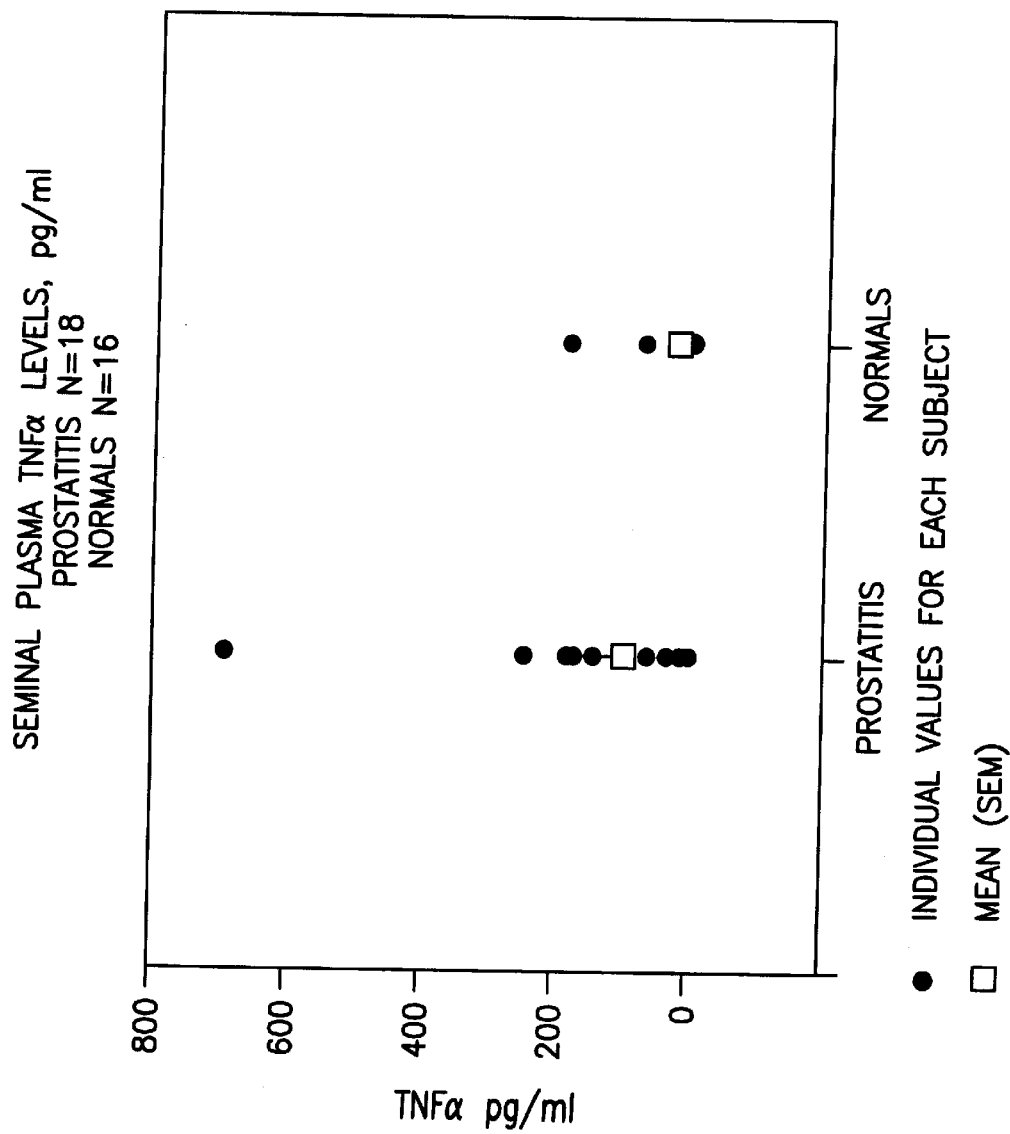
FIG. 3 shows the seminal plasma TNF-α levels as measured by the sandwich ELISA.
Figure 4:
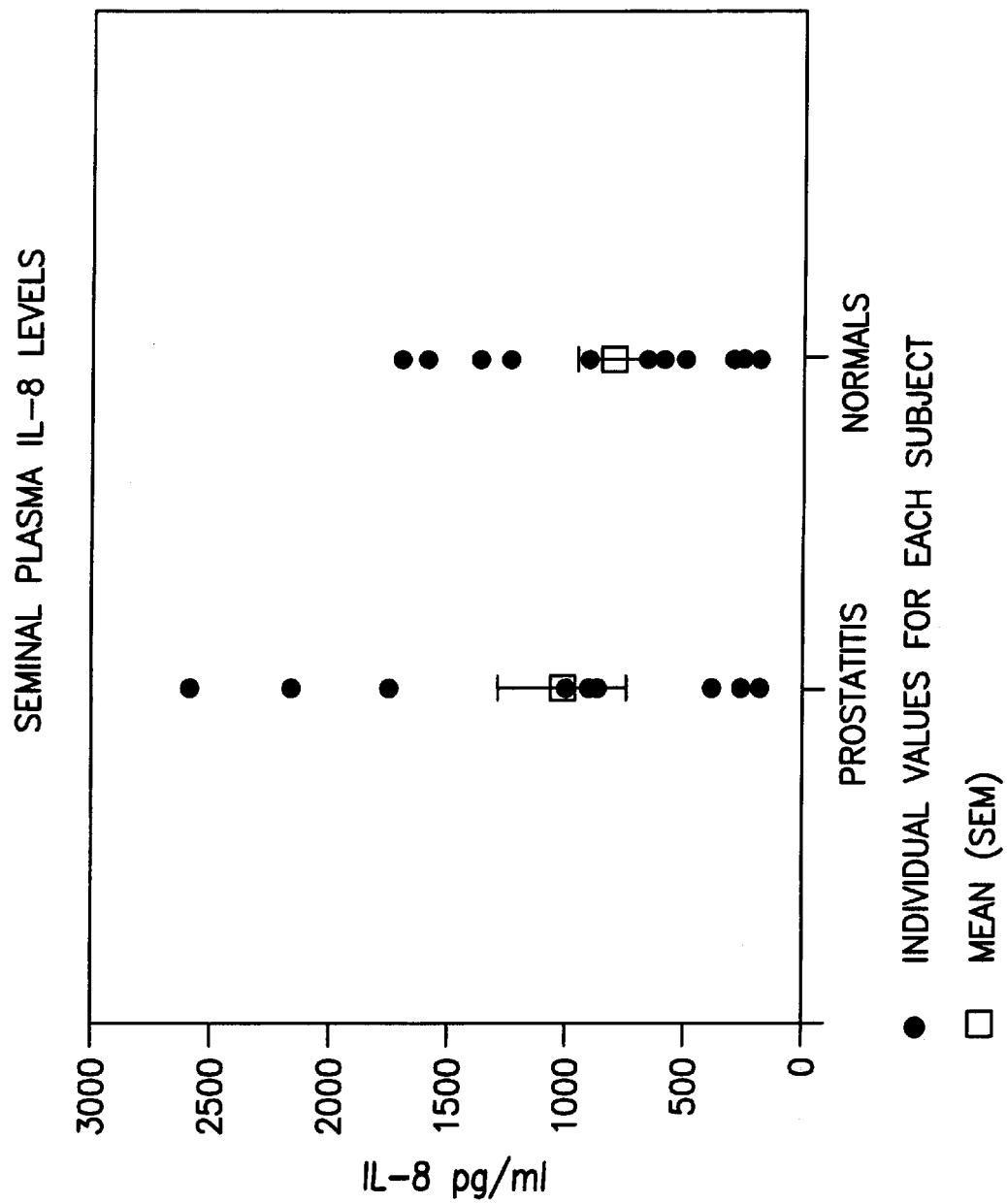
FIG. 4 shows the seminal plasma IL-8 levels as measured by the sandwich ELISA.
Figure 5:
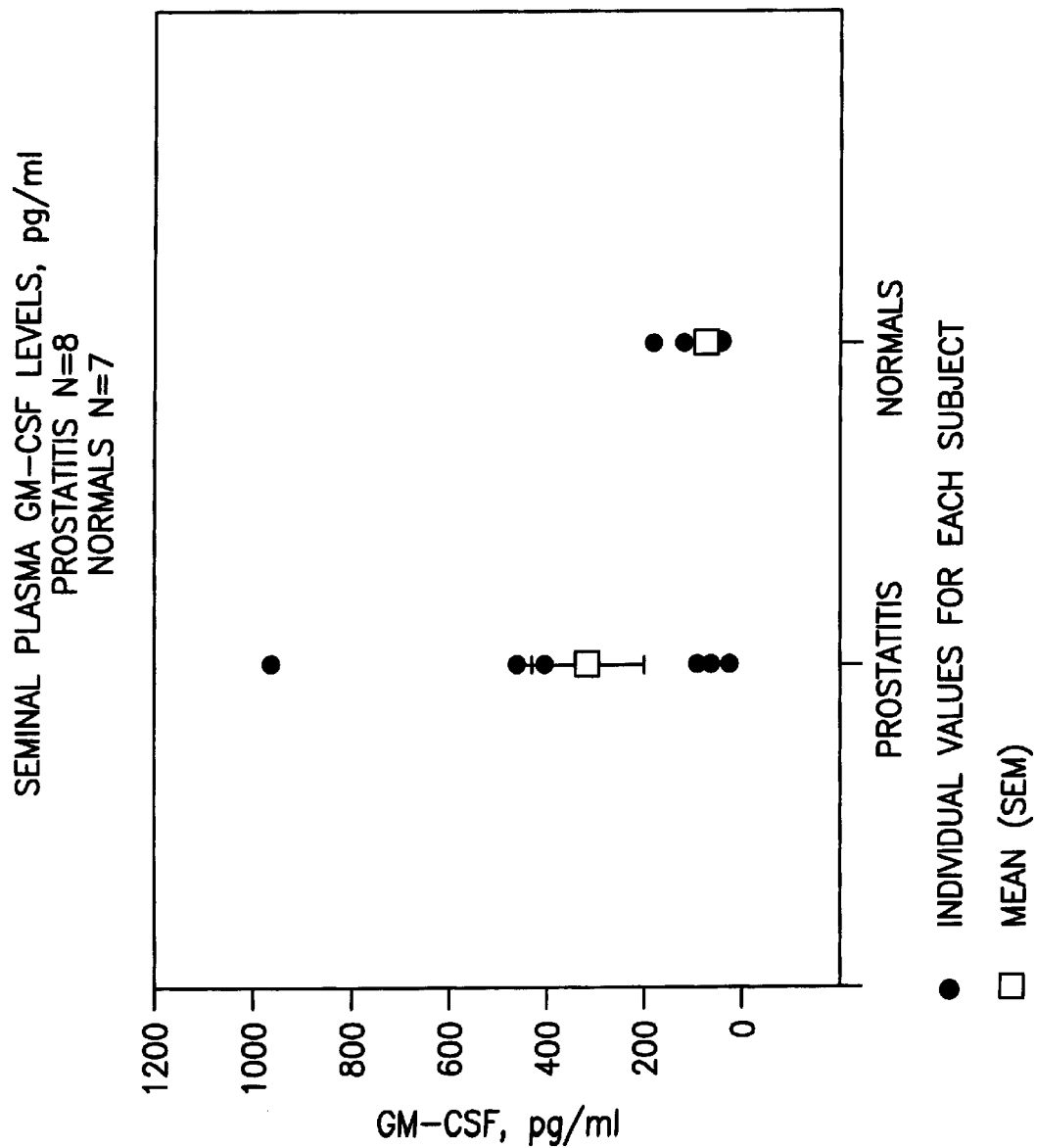
FIG. 5 shows the seminal plasma GM-CSF levels as measured by the sandwich ELISA.
Figure 6:
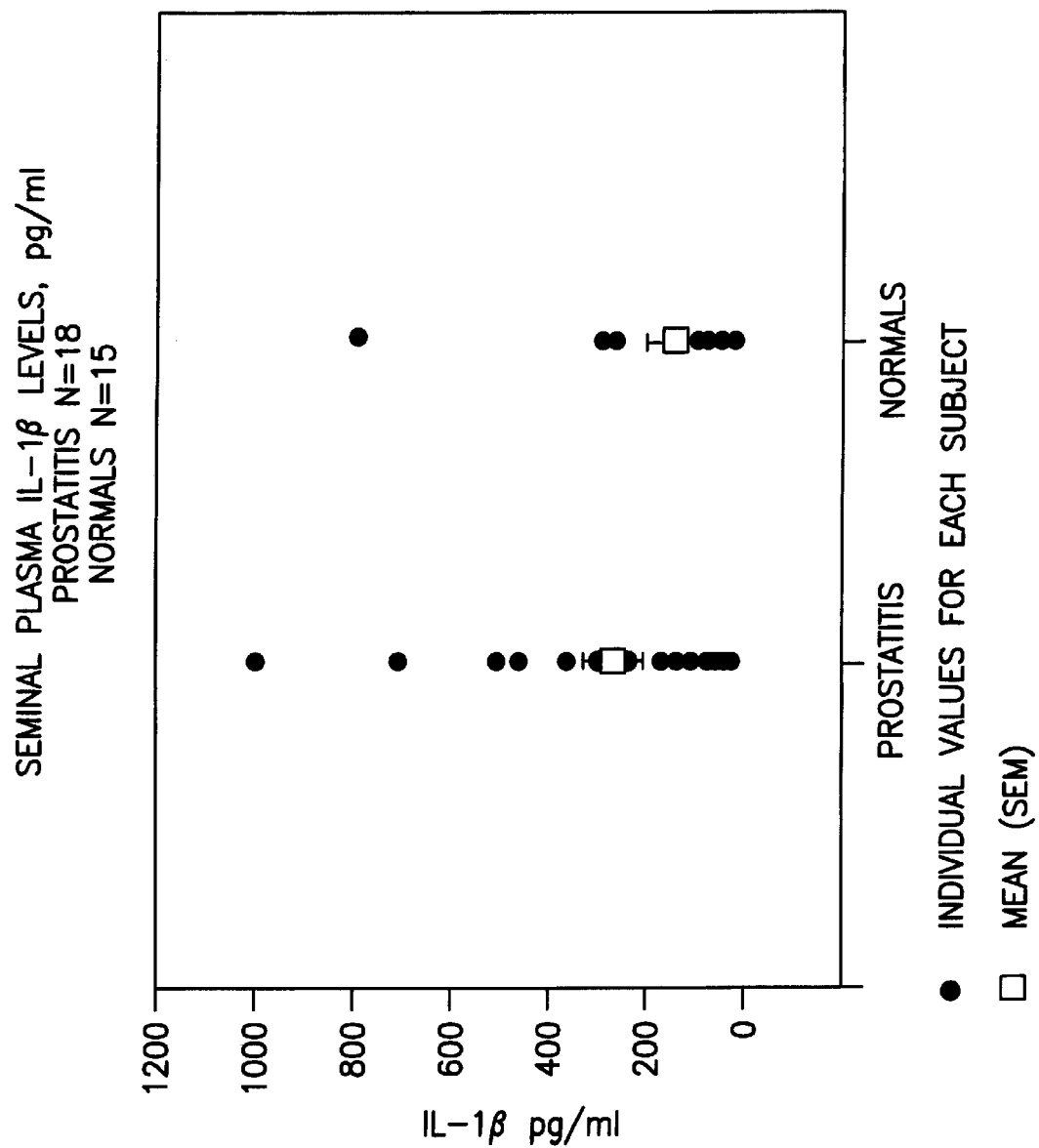
FIG. 6 shows the seminal plasma IL-1β levels as measured by the sandwich ELISA.
Figure 7:
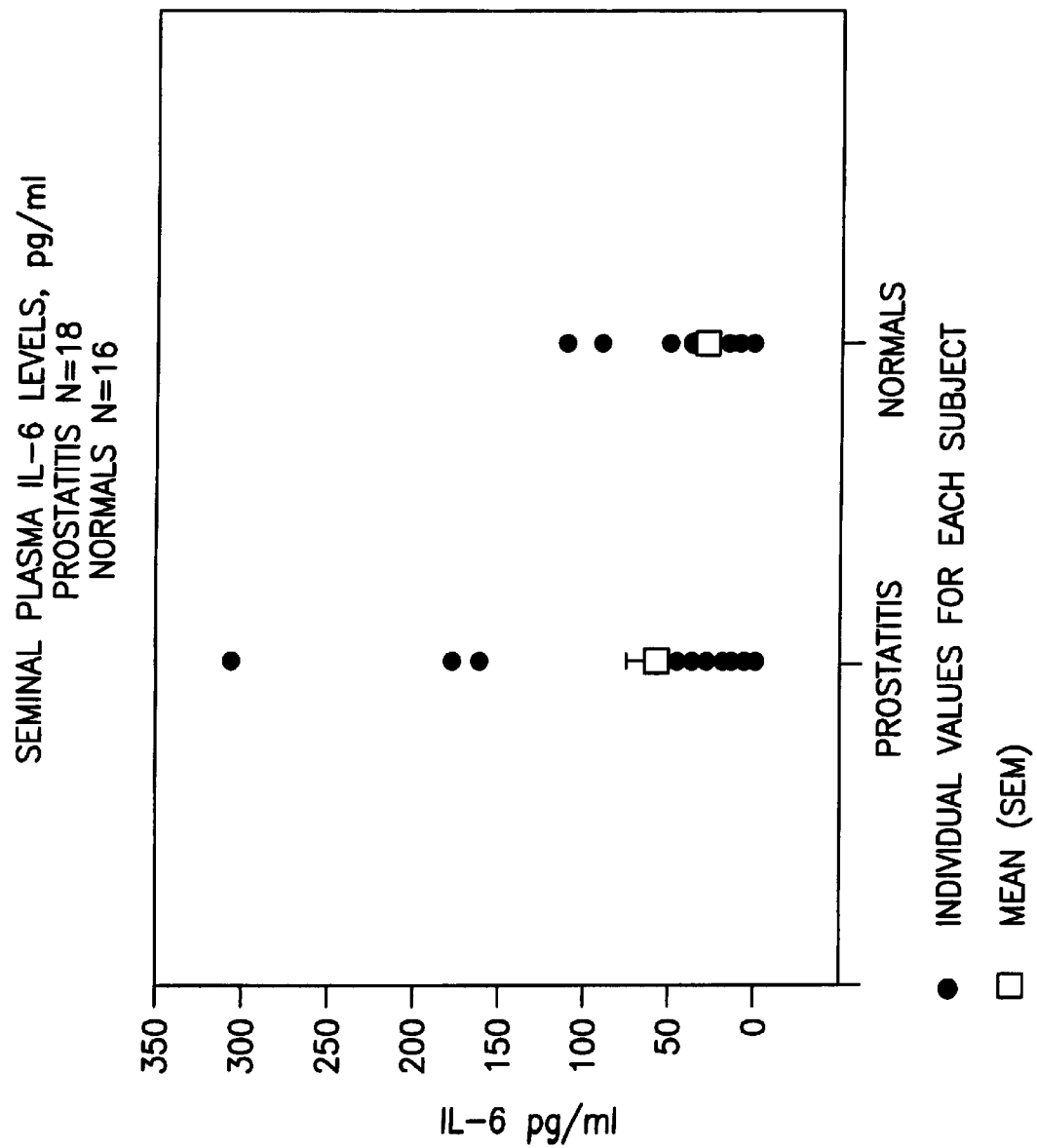
FIG. 7 shows the seminal plasma IL-6 levels as measured by the sandwich ELISA.

The results of the proliferation assay are shown in FIG. 1. The mean SEM (counts per minute) for the proliferation assay are shown in FIG. 2. These data show that a subpopulation of men with CPPS had a significant recall proliferative response to seminal plasma pulsed PBMCs, and that this response was not observed in the control group. Both normal subjects and patients with CPPS had equivalent and significant responses to the recall antigens tetanus toxoid and *Candida* extract. The recall response to seminal plasma was dose-dependent and the antigen appears to be contained within the secretions of the prostate. A similar recall response was observed when the seminal plasma was obtained from men with seminal vesicle atresia or from normal male volunteers.

The data clearly show that an autoimmune response to self prostatic proteins is occurring in men with the clinical syndrome of CPPS. The antigenic material in seminal plasma is presumably processed and presented by antigen-presenting cells in PBMCs.

To further characterize the observed autoimmune response, the present inventors analyzed seminal plasma for the presence of cytokines. Measurement of cytokine levels in the semen of men with CPPS represents an objective measure of genital tract inflammation as cytokines are mediators of the inflammatory response.

The pattern of seminal cytokines observed so far suggests that macrophage products proximal in the inflammatory cytokine cascade are elevated in men with chronic non-bacterial prostatitis. The T-cell cytokine IFN-γ was not detected in controls or CPPS patients (data not shown). The correlation of IL-1α and TNF-α levels (FIG. 8) strongly suggests that these cytokines are physiologically present in the semen because of some stimulus.

Elevated levels of TNF-α in these patients is particularly intriguing. TNF-α is a critical proximal mediator in several known autoimmune conditions including rheumatoid arthritis and Crohn's disease. Recent prospective, randomized, blind trials in these two diseases have clearly shown that blocking TNF-α with antibodies or receptor antagonists improves symptoms and signs of these diseases in patients [Moreland et al., *N.Engl.J.Med.* 337:141–47 (1997); Targan et al., *N.Engl.J.Med.* 337:1029–35 (1997)].

The inventors have discovered that cytokines useful in the diagnosis of CPPS include GM-CSF, IL-1-β, IL-8, IL-6, and TNF-. However, it will be apparent to those in the art that it is a routine matter in light of the instant disclosure to test seminal fluid of subjects with CPPS symptoms for all known cytokines to determine whether further cytokines are elevated in such subjects.

The most sensitive method ever applied to detect circulating human TNF-α, based on extremely high binding specificity and affinity of the p55 TNF-α receptor for TNF-α, failed to detect any circulating TNF-α protein in healthy humans [Poltorak et al., *J. Immunol. Methods* 169:93–99 (1994)]. The detection limit of this assay is 200 attomolar ($10^{-18}$ mol $L^{-1}$), which equals 120,000 TNF-α trimers or 10 femtograms in 1 ml plasma. By contrast, in acute diseases such as septic shock, TNF-α circulates in nanomolar ($10^{-9}$ mol $L^{-1}$) concentrations.

Methods for Diagnosing CPPS

The methods of the subject invention exploit the inventors' discovery of the relationship between cytokine levels in seminal plasma to CPPS. The inventors have shown that cytokines are secreted in measurable quantities in the semen of men with CPPS, and hence can be used for diagnostic purposes. The diagnostic methods of the present invention provide a more objective, accurate, and quantifiable measure of inflammation in the prostate of men with CPPS.

Collection of semen from men suspected of having CPPS may be accomplished via any known method. Semen is preferably incubated at ambient temperature for 30 minutes, followed by centrifugation, results in the recovery of supernatant, referred to herein as "seminal plasma." Cytokine levels are preferably measured in this seminal plasma, but may also be measured in other semen components or fractions, such as expressed prostatic secretions Cytokine assay of the seminal plasma may be accomplished by any known method for identifying and quantifying a protein or peptide in a body sample. Preferred assays are immunoassays, such as radioimmunoassays. The most preferred method is the sandwich enzyme-linked immunosorbant assay (ELISA) employing commercially available monoclonal antibodies. Various receptor binding assays may also be employed in the diagnostic methods of the present invention.

Methods for Treating CPPS

The invention also provides a method for treating men determined to be suffering from a disorder associated with elevated levels of one or more cytokines in one or more components or fractions of semen, preferably seminal plasma, comprising administering one or more anti-cytokine agents, such as anti-TNF-α agents. In preferred embodiments of the claimed methods, the anti-cytokine agent is administered to a patient suffering from a disorder falling within the definition of CPPS, including prostatitis.

The anti-cytokine agent may be provided in a formulation suitable for administration to a patient. Such formulations are known in the art and depend on the chemical and physiological characteristics of the particular anti-cytokine agent.

The dosage regimen is readily determined by one of skill in the art, taking into account various factors which affect the action of the particular anti-TNF-α agent. For example, dosage may vary depending on the condition, type and/or severity of damaged tissue; the patient's age and/or diet; time, mode, and/or route of administration, as well as other clinical factors known in the art. Generally, systemic or injectable administration, such as intravenous (IV), intramuscular (IM) or subcutaneous (Sub-Q) injection, will be initiated at a dose which is minimally effective. The dose will then be gradually increased until a positive effect is observed. Incremental increases should be continued, so long as such increases produce a corresponding increase in effect, while taking into account any adverse affects that may appear. The addition of any other anti-TNF-α agents to the final composition may also affect the final dosage. Progress may be monitored by analyzing the cytokine levels by the diagnostic assay previously described in the subject invention.

Anti-Cytokine Agents

Compounds which interfere with the production and/or activity of various cytokines, such as TNF-α, are widely known. The term "anti-cytokine compound" as used herein includes compounds which inhibit production, processing or activity of a cytokine or its receptor. Likewise, the term "anti-TNF-α compound" as used herein includes compounds which inhibit production, processing or activity TNF-α or its receptor(s). Such compounds may, for example, bind to the cytokine or its receptor, thereby preventing the natural cytokine-receptor interaction.

Many anti-TNF-α compounds are known and/or are under development for treatment of other conditions associated with TNF-α, such as rheumatoid arthritis, insulin dependent diabetes, sepsis and Crohn's disease [see Haworth et al., "Cytokine and Anti-Cytokine Therapy", *The Cytokine Handbook*, Thomson, Angus, ed., pp. 777–801 (1998)]. Synthesis of TNF-α can be inhibited by a variety of known agents, including phosphodiesterase inhibitors, prostanoids, adenosine, corticosteroids and IL-10. Glucocorticoids and prostaglandin $E_2$ ($PGE_2$) also inhibit TNF synthesis. Processing of the TNF-α pro-protein can be inhibited by specific inhibitors of the TNF-α metalloprotease. The effects of released TNF-α protein can be antagonized by TNF-α antagonists, such as soluble TNF-α receptors or anti-TNF-α antibodies.

Anti-TNF-α agents which can be used in the methods of the subject invention also include various cytokines, endogenous mediators, and synthetic drugs. Cytokines useful as anti-TNF-α agents include, for example, IL-4, IL-10, TGFβ, and ciliary neurotrophic factor.

Endogenous mediators which can be used as anti-TNF-α agents include, for example, corticosteroids, prostanoids, adenosine, histamine, nitric oxide, retinoic acid, and n-3 polyunsaturated fatty acids.

Synthetic drugs useful in the methods of the present invention as anti-TNF-α agents include, for example, pentoxifylline, rodipram, cyclosporin A, chlorpromazine, thalidomide, antisense oligonucleotides, tetravalent guanylhydrazone (CNI-1493), and bicyclic imidazoles (SK&F 86002).

Compounds which inhibit TNF processing include, for example, compound 2, and GI 129471.

Compounds which inhibit TNF-α effects useful according to the present invention include, for example, anti-TNF-α antibodies and soluble TNF receptors, and TNF receptor chimeras.

Inhibition of TNF synthesis can be achieved by several means: (1) inhibition of transcription; (2) decrease of the mRNA half-life; and (3) inhibition of translation. Phosphodiesterase inhibitors pentoxifylline act mainly on transcription. Dexamethasone inhibits translation. Thalidomide specifically decreases the half-life of TNF mRNA. Furthermore, antisense oligonucleotides allow specific suppression of TNF translation.

Phosphodiesterase inhibitors are also known to suppress TNF activity. Among the clinically used phosphodiesterase inhibitors, pentoxifylline has been the most extensively studied with regard to TNF-suppressing activity. Patients receiving anti-CD3 mAbs to treat acute graft rejection have been administered pentoxifylline to decrease harmful TNF synthesis. Rolipram, a specific type IV phosphodiesterase inhibitor, is 500-fold more potent than pentoxifylline at suppressing TNF synthesis. Type IV phosphodiesterase is predominant in monocytes and is therefore an excellent target for suppression of cAMP-sensitive functions in this cell type. Moreover, rolipram synergizes with prostanoids (prostaglandin $E_2$ ($PGE_2$), prostacyclin analogs) both in elevating cAMP concentrations and in suppressing TNF synthesis. This may confer a tropism towards inflamed tissue with high interstitial concentrations of PGE$_2$. Several animal studies show the efficacy of specific phosphodiesterase inhibition in vivo: in a rat model of experimental autoimmune encephalomyelitis (EAE), TNF suppression and amelioration by rolipram was confirmed for EAE in non-human primates (marmosets); and suppression of TNF synthesis and enhanced survival has been demonstrated following rolipram treatment in a rat model of acute respiratory distress syndrome. Rolipram was first synthesized in the early 1980s. It has been tested in clinical trials as an antidepressant but has not been marketed.

In a preferred aspect of the present invention, the anti-chemokine compound is etanercept, a dimeric fusion protein marketed under the name ENBREL. Etanercept consists of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. Etanercept is produced by recombinant DNA technology in a Chinese hamster ovary (CHO) mammalian cell expression system. Etanercept consists of 934 amino acids and has an apparent molecular weight of approximately 150 kilodaltons. Etanercept is preferably supplied as a sterile, white, preservative-free, lyophilized powder for parenteral administration after reconstitution with 1 mL of the supplied Sterile Bacteriostatic Water for Injection, USP (containing 0.9% benzyl alcohol). Following reconstitution, the solution of etanercept is preferably clear and colorless, with a pH of 7.4±0.3. Each single-use vial of etanercept preferably contains 25 mg etanercept, 40 mg mannitol, 10 mg sucrose, and 1.2 mg tromethamine.

The patents listed in Table 2, in Section 6.4 of the present application describe various illustrative anti-cytokine compounds which are also within the scope of the present invention.

Compositions Comprising Anti-TNF Agents and Modes of Administration

EXAMPLES

The following examples are intended to illustrate but not limit the invention.

All subjects were required to fulfill the NIDDK Prostatitis Workshop criteria for CPPS. For every protocol included an age and race-matched control group without CPPS symptoms.

EXAMPLE 1: Determination of Seminal Plasma Reactivity in CD4$^+$ Cells

Seminal Plasma Used as Principal Source of Antigen

Normal seminal plasma was used as the principal source of antigen. This material was obtained from pooled normal semen donors examined in the University of Maryland Andrology/In Vitro Fertilization laboratory. Semen was used for these studies if the semen analysis showed normal sperm count, motility, volume, pH and liquefaction and no leukospermia. Semen from normal donors was allowed to liquefy by incubation for 30 minutes at room temperature and centrifuged to remove spermatozoa. The supernatant was diluted in PBS and filter sterilized through a 0.2 $\mu$m filter and cryopreserved at 70° C. in aliquots. Several specimens were pooled and frozen in aliquots to allow for multiple experiments. Seminal plasma preparations were tested for endotoxin by the Limulus amebocyte lysis (LAL) assay. It was ensured that endotoxin levels in semen were low and standardized between lots of pooled seminal plasma. Control antigens were tetanus toxoid and candida extract.

CD4$^+$ Proliferation Assay

Recall antigen proliferation assays were performed on CD4$^+$ T lymphocytes from the PBMC of all subjects enrolled in the protocol as described previously [Cohen et al., *J. Immunother.* 14:242–252 (1993)]. Complete medium (CM) consists of RPMI-1640 containing 10% pooled human serum plus penicillin/streptomycin. PBMC was produced from leukopheresis packs by centrifugation over Lymphocyte Separation Medium. Aliquots of PBMC were cryopreserved in 10% DMSO in human serum avoiding exposure to potential bovine antigens in fetal bovine serum. Human serum from males may contain prostatic antigens, such as PSA. However, PSA is present in normal male serum in low amounts and all comparisons of reactivity to antigen are made to unpulsed antigen presenting cells cultured in the same medium alone. Hence any effect of traces of prostate antigens in human serum cannot explain differences between pulsed and unpulsed groups. PBMC was enriched for CD4$^+$ T cells by immunoaffinity column chromatography by negative selection (R & D Systems, Minneapolis, Minn.). This was the responding population.

The stimulator cells consisted of autologous whole PBMC pulsed with various dilutions of pooled human seminal plasma, salt cut proteins, purified prostatic proteins or control antigens in CM for 18 hours. Antigens were added to 3×10$^6$ PBMC/well in 24 well plates containing 2 ml CM/well. Dilutions of seminal plasma and control antigens from 1:50 to 1:500 were used to determine antigen dose. Pulsed APC was washed, irradiated (3000 cGy, $^{137}$Cs source) and mixed with the responder population in triplicate in 96 well plates at various stimulator:responder ratios. APC alone and T cells alone were set up as controls. Other wells received PHA 1 $\mu$g/ml or PHA plus unpulsed PBMC to ensure that the responder population can proliferate. The plates were incubated for 5 days at 37° C. and $^3$H-thymidine 1 $\mu$Ci/well was added for the last 18 hours of the incubation. The cells were then harvested onto filtermats and the incorporated counts per minute (CPM) in the cells determined by liquid scintillation counting with the BetaPlate instrument (Wallac, Gaithersburg, Md.).

Data were analyzed by determining the mean of triplicate wells. CPM from stimulator PBMC alone was subtracted. A patient was considered a responder to seminal plasma if the mean CPM obtained from seminal plasma-pulsed APC exceeds the mean plus 3 standard deviations of the CPM obtained from unpulsed APC. Differences between the response of subjects within a group (prostatitis, normal volunteer) to recall and seminal plasma antigens was evaluated by the Wilcoxon Signed-Ranks test. This is a non-parametric test appropriate for a response which is not normally distributed as our preliminary data show for the response to seminal plasma. Differences in the overall mean CPM response to the antigens compared between groups (prostatitis versus normal, for example) was performed by the Wilcoxon Rank Sum test. A 2 tailed p value of less than 0.05 was interpreted as excluding the null hypothesis for each comparison.

The results of these experiments are shown in FIGS. 1 and 2.

EXAMPLE 2: Measurement of Inflammatory Cytokine Levels in Semen

Semen Collection

Semen was obtained by masturbation into a sterile container. Subjects were abstinent for 3 days prior to sample collection. Semen was allowed to liquefy by incubation at ambient temperature for 30 minutes and then centrifuged. The supernatant seminal plasma was collected and frozen at −30° C. in aliquots until cytokine assay were performed.

Sandwich ELISA for Cytokines in Semen and Culture Supernatants

Two-antibody ELISAs were performed using commercially available paired monoclonal antibodies and recombinant standards (cytokines IL-8, GM-CSF, IL-1β, IL-6 and TNF-α were purchased from Endogen). Cytokine capture antibodies diluted in PBS were coated in polystyrene microtiter plates (Maxisorb; Nunc, Denmark) overnight at 25° C. and blocked for 2 hours with PBS containing 2% BSA and 12 mg/ml casein (Sigma) and 0.01% thimerosal. The plate was washed with TBS/Tween and 50 μl assay buffer (PBS/4% BSA/0.01% thimerosal) was added to each well.

Based on preliminary experiments, samples were diluted with PBS to adjust cytokine concentrations within the detection range of each cytokine ELISA assay. Diluted samples and recombinant standards (50 μl/well) were incubated in duplicate for 2 hours at 37° C. After thorough washing with PBS/Tween, 100 μl biotinylated detecting antibodies diluted in assay buffer were added to each well and incubated for 1 hour at 25° C.

After washing with PBS/Tween, 100 βl of streptavidin horseradish peroxidase conjugate (Dako) was added to each well for 45 min at 25° C. After a final washing, 100 ml commercially prepared peroxidase substrate (Dako) was added for approximately 30 minutes until optimal color change in the standards wells is noted. After the reaction was stopped with 100 ml 2N HCI, the absorption at 450 (minus absorption at 630 nm) was measured using a Dynatech MR 4000 microplate reader (Chantilly, Va.). The concentration of cytokine was calculated based on a standard curve performed for each plate by fitting a first or second order polynomial equation to the data using Deltagraph (Deltapoint) on a Macintosh computer. Assay reliability was monitored by including an internal control with each assay.

The results of these experiments are shown in FIGS. 3–8.

EXAMPLE 3: Effects of Administration of Prednisone on Patients with CPPS

To test the methods of the present invention, subjects with negative localization studies were started on a 30 day course of oral prednisone 60 mg once a day. Subject 1 began steroids on May 26, 1998, and stopped early (Jun. 16, 1998) dues to side effects. Subject 2 began steroids on May 26, 1998, and completed the course on approximately Jun, 24, 1998. Subject 3 began steroids on Jul. 22. 1998 and stopped early (Aug. 4, 1998) due to side effects. Subject 4 began steroids on Oct. 13, 1998. Subject 5 began steroids on Sep. 15, 1998 and completed the course on Oct. 15, 1998. All values have been multiplied by the dilution factors. The results are set forth in Table 1:

TABLE 1

Results of 30 Day Course Oral Prednisone 60 mg 1/day

| Patient | visit # | DATE | time in relation to therapy | Age | SFQ 0–50 | SSI 0–100 | IL-1B 1.56–100 pg/ml | TNF-a 3.9–250 pg/ml |
|---|---|---|---|---|---|---|---|---|
| SUBJECT 1 | 0 | 4/24/98 | pre | 57 | 28 | 51 | 148 | 346 |
|  | 1 | 6/9/98 | mid |  | 31 | 59 | 118 | 280 |
|  | 2 | 6/12/98 | end |  | 29 | 42 | 140 | 364 |
|  | 3 | 8/7/98 | post |  | 23 | 35 | 84 | 184 |
| SUBJECT 2 | 0 | 5/1/98 | pre | 43 | 21 | 37 | 32 | 44 |
|  | 1 | 5/26/98 | mid |  | 10 | 15 | 8 | 26 |
|  | 2 | 6/12/98 | end |  | 15 | 17 | 15 | 45 |
|  | 3 | 6/18/98 | post |  | 23 | 32 | 3 | 8 |
|  | 4 | 7/7/98 | post |  | 23 | 17 | 3 | 14 |
| SUBJECT 3 | 0 | 7/22/98 | pre | 40 | 9 | 31 | 4 | 8 |
|  | 1 | 8/3/98 | mid |  | 16 | 27 | 19 | 12 |
|  | 2 | 9/8/98 | post |  | 7 | 18 | 2 | 8 |
| SUBJECT 4 | 0 | 10/13/98 | pre | 34 | 32 | 14 | 112 | 22 |
|  | 1 | 10/27/98 | mid |  | 13 | 3 | 40 | 109 |
|  | 2 | 11/13/98 | end |  | 12 | 0 | 36 | 27 |
|  | 3 | 2/3/99 | post |  | 5 | 7 | 4 | 14 |
| SUBJECT 5 | 0 | 9/15/98 | pre | 24 | 34 | 64 | 110 | 284 |
|  | 1 | 9/25/99 | mid |  | 33 | 65 | — | — |
|  | 2 | 10/23/98 | end |  | 24 | 42 | 57 | 154 |

Seminal plasma was prepared by centrifugation of semen sample at 1500 rpm for 10 min and harvesting the supernatant. Seminal plasma was frozen away at −30° C. All samples were diluted 2× in PBS and subjected to cytokine analysis without any further dilutions. Samples were submitted as 125 ul aliquots for each cytokine. Cytokine analysis was done in duplicates using 50 ul of sample per well.

The score of the Symptoms Frequency Questionnaire (SFQ) increases with the frequency of symptoms. The score of the Symptom Severity Index (SSI) increases with the severity of the symptoms. The symptom indices used in the studies are described in J. C. Nickel and R. Sorensen. Transurethral microwave thermotherapy for nonbacterial prostatitis: A randomized double-blind sham controlled study using new prostatitis specific assessment questionnaires. *J. Urol.* 155 (6): 1950–1954,1996.

The results demonstrate that anti-TNF-α therapy can reduce both the severity and the frequency of symptoms of CPPS.

Exemplary Anti-Cytokine Compounds

The patents listed in Table 2 below describe various illustrative anti-cytokine compounds which are also within the scope of the present invention. Other such patents are available in various patent databases, such as the Lexis-Nexis patent database, by searching, e.g.,using a boolean search such as "chemokine /2 (antagoni! or inhibit!)" or similarly, "TNF /2 (antagoni! or inhibit!)", where "!" is a universal character which allows any combination of additional letters.

TABLE 2

Exemplary Anti-Cytokine Compounds

| Patent No. | Issue Date | Title | Abstract |
| --- | --- | --- | --- |
| 5,900,434 | May 4, 1999 | Method for inhibiting the production of interleukin-1 or tumor necrosis factor-alpha by administering acanthoic acid | Process for the preparation of (−)-pimara-9(11),15-diene-19-oic acid(acanthoic acid) and pharmaceutical compositions comprising acanthoic acid useful for the treatment of diseases caused by an excessive production of interleukin-1 or tumor necrosis factor-alpha. |
| 5,900,430 | May 4, 1999 | Cytokine inhibitors | Invented are methods of inhibiting the production of cytokines, particularly inhibiting the production of interleukin-1 and inhibiting the production of tumor necrosis factor in a mammal in need thereof which comprises administering to such mammal an effective amount of an azaspirane derivative. |
| 5,900,417 | May 4, 1999 | 1,3,3-(Trisubstituted)cyclohexane monomers and related compounds | This invention relates to certain 1,3,34-(trisubstituted)cyclohexane monomers and related compound which are useful in treating allergic and inflammatory diseases and for inhibiting the production of Tumor Necrosis Factor (TNF). |
| 5,892,098 | Apr. 6, 1999 | 3,3-(disubstituted)cyclohexan-1-one monomers and related compounds | This invention relates to derivatives of 3,3-(disubstituted)cyclohexan-1-one monomers and related compounds which are useful for treating allergic and inflammatory diseases. |
| 5,891,924 | Apr. 6, 1999 | Curcumin (diferuloylmethane) inhibition of NF kappa B activation | The present invention provides a method of inhibiting the activation of the NF kappa B transcription factor in an animal in need of such treatment comprising the step of administering to said animal a pharmacologically effective dose of curcumin. Also provided is a method of inhibiting the nuclear translocation of the p65 subunit of the NF kappa B transcription factor in a cell or in an animal in need of such treatment comprising the step of administering to said animal a pharmacologically effective dose of curcumin. |
| 5,891,883 | Apr. 6, 1999 | 4,4-(disubstituted)cyclohexan-1-ols monomers and related compounds | The present invention relates to 4,4(disubstituted)cyclohexan-1-ol monomers and related compounds, pharmaceutical compositions containing these compounds, and their use in treating allergic and inflammatory diseases and for inhibiting the production of Tumor Necrosis Factor (TNF). |
| 5,891,878 | Apr. 6, 1999 | Quinolones and their therapeutic use | 1-Alkyl-substituted-quinolone-3-carboxamides have therapeutic utility via inhibition of Phosphodiesterase IV esterase and/or Tumour Necrosis Factor activity. The compounds of the invention have the general formula (I): [See Original Patent for Chemical Structure Diagram] (I) The compounds of the invention encompassed by formula (I) include enantiomers, diastereoisomers and mixtures, including racemic mixtures. |
| 5,891,675 | Apr 6, 1999 | TNF receptor death domain ligand proteins | Novel TNF receptor death domain ("TNF-R1-DD") ligand proteins are disclosed Polynucleotides encoding the TNF-R1-DD ligand protein are also disclosed along with vectors, host cells, and methods of making the TNF-R1-DD ligand protein Pharmaceutical compositions containing the TNF-R1-DD ligand protein methods of treating inflammatory conditions, and methods of inhibiting TNF-R death domain binding are also disclosed. Methods of identifying inhibitors of TNF-R death domain binding and inhibitors identified by such methods are also disclosed. |
| 5,891,618 | Apr. 6, 1999 | Method for quantifying LBP in body fluids | The present invention provides a method for quantifying the presence of extracellular LBP in body fluids including blood in a subject comprising conducting an LBP immunoassay on plasma obtained from said subject. |
| 5,891,432 | Apr. 6, 1999 | Membrane-bound cytokine compositions comprising GM = CSF and methods of modulating an immune response using same | The present invention provides a cellular vaccine having a membrane-bound fusion protein that includes a non-antibody immunomodulatory molecule such as GM-CSF operatively fused to a heterologous membrane attachment domain. Non-antibody immunomodulatory molecules useful in the invention include immunostimulatory and immunosuppressive molecules such as cytokines. In one embodiment, the invention provides a cellular vaccine having a membrane-bound fusion protein that includes a non-antibody immunomodulatory molecule operatively fused to a heterologous membrane attachment domain and, additionally, a disease-associated antigen or immunogenic epitope thereof. Further provided by the invention are methods of modulating an immune response against a disease-associated antigen by administering to an individual a cellular vaccine having a membrane-bound fusion protein that includes a non-antibody immunomodulatory molecule operatively fused to a heterologous membrane attachment domain. |
| 5,889,011 | Mar. 30, 1999 | Substituted amino alkyl compounds | Compounds and pharmaceutical compositions thereof comprise the formula: (R)j- (core moiety), including resolved enantiomers and/or diastereomers, hydrates, salts, solvates and mixtures thereof, wherein J is an integer from one to three, the core moiety is non-cyclic or comprises at least one, five- to seven-membered ring structure, R may be selected from the group consisting of hydrogen, halogen, hydroxyl, amino, substituted or unsubstituted benzyl, alkyl (C[1–6]) or alkenyl (C[1–6]), and at least one R has the formula [See Original Patent for Chemical Structure Diagram] I wherein n is an integer from four to eighteen; each R'1 and R'2 is independently hydrogen, alkyl (C[1—4]) or alkenyl (C[1–4]), the alkyl or alkenyl groups being preferably substituted by a halogen, hydroxyl, ketone or dimethylamino group and/or may be interrupted by an oxygen or hydrogen atom or an alkyl (C[1–4]) group; and each R'3 and R'4 is independently hydrogen or methyl. Preferably, n is an integer from six to ten, R'1 and R'2 are independently hydrogen or methyl and R'3 and R'4 are hydrogen. The compounds are useful in treating or preventing for example sepsis syndrome, hematopoietic or organ toxicity, baldness, hair loss or alopecia caused by cytotoxic therapies, and progression of an inflammatory or autoimmune disease. |
| 5,888,977 | Mar. 30, 1999 | Therapeutic uses of BPI protein products for human meningococcemia | Methods and materials for the treatment of human meningococcemia are provided in which therapeutically effective amounts of BPI protein products are administered. |

TABLE 2-continued

Exemplary Anti-Cytokine Compounds

| Patent No. | Issue Date | Title | Abstract |
|---|---|---|---|
| 5,886,010 | Mar. 23, 1999 | TNF- alpha inhibitor | A method for the prophylaxis and treatment of diseases induced by accelerated INF-alpha secretion, such as rheumatoid arthritis, endotoxin shock, adult respiratory distress syndrome, thermal burn, asthma, myocardial infarction, acute phase of viral myocardiosis, etc. which comprises administering a carbostyril compound of the formula: [See Original Patent for Chemical Structure Diagram] [I] wherein $R_1$ is H or lower alkyl, and $R_2$ is phenyl(lower)alkyl having optionally 1 to 3 lower alkoxy substituents on the phenyl ring, or a pharmaceutically acceptable salt thereof to a subject. |
| 5,883,131 | Mar. 16, 1999 | Cyclic sulfone derivatives | A compound of the formula [See Original Patent for Chemical Structure Diagram] I wherein n, p, q, X, Y, Z and Ar are as defined herein, useful in the treatment of arthritis, cancer, tissue ulceration, restenosis, periodontal disease, epidermolysis bullosa, scleritis or other diseases characterized by matrix metalloprotenase activity, as well as AIDS, sepsis, septic shock or other diseases involving the production of TNF. |
| 5,877,222 | Mar. 2, 1999 | Method for treating aids-associated dementia | The invention comprises inhibiting expression of TNF- alpha by administering an effective amount of a stabilized activated oxygen in a matrix of chlorite ions. Preferably, a pharmaceutically acceptable formulation of tetrachlorodecaoxide is used, and more preferably, WF-10. An effective amount of WF-10 comprises up to about 0.5 ml/kg. Another embodiment of the invention is a method of treating AIDS-associated dementia comprising the step of administering to a human an amount of a stabilized activated oxygen in a matrix of chlorite ions sufficient to inhibit production of TNF- alpha. |
| 5,877,200 | Mar. 2, 1999 | Cyclic amides | Cyclic amides are inhibitors of tumor necrosis factor and can be used to combat cachexia, endotoxic shock, and retrovirus replication. A typical embodiment is 3-phenyl-3-(1-oxoisoindolin-2-yl)propionamide. |
| 5,877,180 | Mar. 2, 1999 | Method for treating inflammatory diseases with A[2a]adenosine receptor agonists | Agonists of A[2a]adenosine receptors are effective for the treatment of inflammatory diseases. |
| 5,877,151 | Mar. 2, 1999 | Method for inhibiting production of tumor necrosis factor | The present invention contemplates a composition and method for treating septic shock in a mammal or as a prophylactic treatment prior to a surgical procedure, comprising administering a therapeutically effective amount of a bacterial lipopolysaccharide binding peptide derived from CAP37 protein. In a preferred version the composition and method of use may comprise a peptide comprising amino acids 20–44 or 120–146 of CAP37 or subunits thereof. |
| 5,874,448 | Feb 23, 1999 | Substituted 2-(2,6 dioxo-3-fluoropiperidin-3-yl) isoindolines and method of reducing TNF alpha levels | 1-Oxo-2-(2,6-dioxo-3-fluoropiperidin-3-yl)isoindolines and 1,3-dioxo-2-(2,6-dioxo-3 fluoropiperidin-3-yl)isoindolines reduce the levels of TNF alpha in a mammal. A typical embodiment is 1,3-dioxo-2-(2,6-dioxo-34luoropiperidin-3-yl-isoindoline. |
| 5,872,146 | Feb. 16, 1999 | Mercapto alkyl peptidyl compounds having MMP and TNF inhibitory activity | Described herein are compounds of formula (I): [See Original Patent for Chemical Structure Diagram] (I) which have MMP and TNF inhibitory activity. |
| 5,869,677 | Feb. 9, 1999 | 3,3-(disubstituted)cyclohexan-1-carboxylate monomers and related compounds | The present invention relates to novel 3,3-(disubstituted)cyclohexan-1-carboxylate monomers and related compounds, pharmaceutical compositions containing these compounds, and their use in treating allergic and inflammatory diseases and for inhibiting the production of Tumor Necrosis Factor (TNF). |
| 5,869,660 | Feb. 9, 1999 | Process of preparing imidazole compounds | Novel 1,4,5-substituted imidazole compounds and compositions for use in therapy as cytokine inhibitors. |
| 5,869,612 | Feb. 9, 1999 | Tumor necrosis factor receptor-associated factors | The invention concerns new tumor necrosis factor receptor associated factors, designated TRAF. The new factors are capable of specific association with the intracellular domain of the type 2 TNF receptor (TNF-R2), and are involved in the mediation of TNF biological activities. |
| 5,869,515 | Feb. 9, 1999 | 1,3-dihydro-2H-imidazol-2-one compounds | The present invention concerns the compounds of formula [See Original Patent for Chemical Structure Diagram] (I) the N-oxide forms, the pharmaceutically acceptable acid or base addition salts and the stereochemically isomeric forms thereof, wherein $R_1$ and $R_2$ each independently are hydrogen; $C_{1-6}$alkyl; difluoromethyl; trifluoromethyl, $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl, bicyclo[2.2.1]heptanyl; $C_{1-6}$alkylsulfonyl; arylsulfonyl; or substituted $C_{1-10}$alkyl, R3 is hydrogen, halo or $C_{1-6}$alkyloxy [See Original Patent for Chemical Structure Diagram] is a bivalent radical of formula [See Original Patent for Chemical Structure Diagram] Alk is $C_{1-4}$alkanediyl; -A-B- is a bivalent radical of formula: -$CR_6$= =$CR_7$- or -$CHR_6$-$CHR_7$-; L is hydrogen; optionally substituted $C_{1-6}$alkyl; $C_{1-6}$alkylcarbonyl; $C_{1-6}$alkyloxycarbonyl; optionally substituted $C_{3-6}$alkenyl; optionally substituted piperidinyl; $C_{1-6}$alkylsulfonyl or arylsulfonyl; aryl is optionally substituted phenyl; Het$_1$ is morpholinyl or optionally substituted pyridinyl, -furanyl, -thienyl, -hydroxypyridinyl, -imidazolyl, -thiazolyl, -oxazolyl, -isoquinolinyl, -quinolinonyl, -piperidinyl, -piperazinyl; and Het$_2$ is morpholinyl or optionally substituted piperidinyl, -piperazinyl, -pyridinyl, -furanyl or -thienyl; having PDE IV and cytokine inhibiting activity. The invention also relates to processes for preparing the compounds of formula (I) and pharmaceutical compositions thereof. |
| 5,869,511 | Feb. 9, 1999 | Isoxazoline compounds as inhibitors of TNF release | This invention relates to isoxazoline compounds of formula (I) which are inhibitors of tumor necrosis factor (TNF). The isoxazoline compounds are useful for inhibiting TNF in a mammal in need thereof and in the treatment or alleviation of inflammatory conditions or disease, including but not limited to rheumatoid arthritis, osteoarthritis, asthma, bronchitis, chronic obstructive airways disease, psoriais, allergic rhinitis, dermatitis and inflammatory bowel disease, sepsis, septic shock, tuberculosis, graft versus host disease and cachexia |

TABLE 2-continued

Exemplary Anti-Cytokine Compounds

| Patent No. | Issue Date | Title | Abstract |
|---|---|---|---|
| | | | associated with AIDS or cancer. This invention also relates to pharmaceutical compositions useful therefor comprising such compounds of formula (I) wherein $X_1$ is —(CH2)[q[OH, —CHOHR$_5$> or —(CH2)[m]CON(R$_6$>) (OH); wherein q and m are each independently 0 or an integer from 1 to 5; R$_5$> is (C1–C4)alkyl; and R$_6$> is hydrogen or (C1–C3)alkyl; n is 0, 1, 2 or 3; $Y_1$ and $Y_2$ are as defined in the application. |
| 5,869,055 | Feb. 9, 1999 | Anti-inflammatory CD14 polypeptides | The invention relates to anti-inflammatory polypeptides comprising soluble CD14 related polypeptides having amino acids at position 7–10 that are different from the native sequence or having amino acids 1–14 deleted. |
| 5,866,717 | Feb. 2, 1999 | Metalloproteinase inhibitors | Compounds of general formula (I), principally characterized in that R4 is a polyether group, are water soluble matrix metalloproteinase inhibitors. [See Original Patent for Chemical Structure Diagram] (I) |
| 5,866,616 | Feb. 2, 1999 | 3,3-(disubstituted) cyclohexan-1-ol monomers and related compounds | The present invention relates to novel 3,3-(disubstituted)cyclohexan-1-ol monomers and related compounds, pharmaceutical compositions containing these compounds, and their use in treating allergic and inflammatory diseases and for inhibiting the production of Tumor Necrosis Factor (TNF). |
| 5,866,570 | Feb. 2, 1999 | Treatment of vascular leakage and related syndrome such as septic shock by administration of metalloproteinase inhibitors | A method for identifying patients at risk of developing vascular leakage syndrome and systemic inflammatory response syndrome (SIRS) such as septic shock by determining the serum levels of metalloproteinase expression, in particular type IV collagenase expression, as well as a method of treating or preventing vascular leakage syndrome and SIRS by the administration of one or more metalloproteinase inhibitors, preferably type IV collagenase inhibitors is taught. Additionally, the therapeutic efficacy of bis(dioxopiperazine) compounds is determined on the basis of collagenase inhibiting activity, and the compounds which inhibit collagenase activity are utilized for the treatment of collagenase related disorders, e.g., vascular leakage syndrome, septic shock, stroke, cardiac disorders, angiogenesis, and arthritis. Finally, a method for preventing or treating toxicity caused by endogenous cytokine expression or cytokine administration or by immunotoxin administration by the administration of one or more metalloproteinase inhibitors preferably type IV cottagenase inhibitors is taught. |
| 5,864,036 | Jan. 26, 1999 | Substituted imidazole compounds | Novel 1,4,5-substituted imidazole compounds and compositions for use in therapy as cytokine inhibitors. |
| 5,864,028 | Jan. 26, 1999 | Degradation resistant mRNA derivatives linked to TNF- alpha ribozymes | This invention describes compounds active against TNF- alpha mRNA. It further describes RNA molecules capable of conferring stability to RNA in vivo through an endogenous ribozyme binding protein(s). Possible mRNA molecules to be stabilized include ribozymes, antisense molecules and mRNA encoding polypeptides useful for protein production. The ribozymes and antisense molecules described herein are useful in mammals and plants, particutarly suited for viral diseases. Methods of production and methods of use are also described. |
| 5,863,949 | Jan. 26, 1999 | Arylsulfonylamino hydroxamic acid derivatives | A compound of formula (I), wherein n, X, R$_3$>, R$_4$> and Ar are as defined above, useful in the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of TNF. [See Original Patent for Chemical Structure Diagram] (I) |
| 5,863,926 | Jan. 26, 1999 | 4,4-(disubstituted)cyclohexan-1-carboxylate monomers and related compounds | The present invention relates to novel 4,4-(disubstituted)cyclohexan-1-carboxylate monomers and related compounds, pharmaceutical compositions containing these compounds, and their use in treating allergic and inflammatory diseases and for inhibiting the production of Tumor Necrosis Factor (TNF). |
| 5,863,786 | Jan. 26, 1999 | Nucleic acid encoding modified human tnf alpha (tumor necrosis factor alpha) receptor | A DNA molecule is provided which encodes a polypeptide which is capable of binding human TNF alpha and which has the first three cysteine-rich subdomains, but not the fourth cysteine-rich subdomain, of the extracellular binding domain of a receptor selected from the 55 kD and 75 kD receptors for human TNF alpha. The ability of the polypeptide to bind to TNF alpha means that it can be used for treating diseases mediated by TNF alpha activity, such as rheumatoid arthritis. |
| 5,861,510 | Jan. 19, 1999 | Arylsulfonyl hydroxamic acid derivatives as MMP and TNF inhibitors | A compound of the formula [See Original Patent for Chemical Structure Diagram] I wherein $R_1$>, $R_2$> $R_3$>, $R_4$> $R_5$>, $R_6$>, $R_7$>, $R_8$>, $R_9$> and Ar are as defined above, useful in the treatment of a condition selected from the group consisting of arthritis, cancer, tissue ulceration, restenosis, periodontal disease, epidermolysis bullosa, scleritis and other disease characterized by matrix metalloproteinase activity, as well as AIDS, sepsis, septic shock and other diseases involving the production of TNF. |
| 5,861,436 | Jan 19, 1999 | Hydroxamic acid derivatives as metalloproteinase inhibitors | The present invention relates to therapeutically active hydroxamic acid derivatives to pharmaceutical compositions containing them, and to the therapeutic use of these compounds. In particular, the compounds are inhibitors of matrix metalloproteinases that are involved in tissue degradation, and in addition, are inhibitors of the release of tumor necrosis factor from cells. |
| 5,861,421 | Jan. 19, 1999 | 4,4-(disubstituted) cyclohexan-1-one monomers and related compounds | This invention relates to derivatives of 4,4-(disubstituted)cyclohexan-1-ones and related compounds which are useful for treating allergic and inflammatory diseases. |
| 5,859,253 | Jan. 12, 1999 | Metalloproteinase inhibitors | L-tert-leucine-2-pyridlyamide or an acid addition salt thereof. |
| 5,859,008 | Jan. 12, 1999 | Arylalkyl diazinones | Arylalkyl diazinone derivatives of the formula I [See Original Patent for Chemical Structure Diagram] I and their physiologically acceptable salts, $R_1$>, $R_2$>, $R_3$>, $R_4$>, Q and X have the meanings indicated in claim 1, exhibit phosphodiesterase IV inhibition |

TABLE 2-continued

Exemplary Anti-Cytokine Compounds

| Patent No. | Issue Date | Title | Abstract |
|---|---|---|---|
| | | | and can be employed for the treatment of inflammatory processes and also of allergies, asthma and autoimmune disorders. |
| 5,856,161 | Jan. 5, 1999 | Tumor necrosis factor receptor-1-associated protein kinase and methods for its use | The present invention provides an isolated and purified protein that associates with the cyloplasmic domain of the p60 form of the tumor necrosis factor receptor, having a molecular weight of about 52–55 kDa on SDS-PAGE, is a phosphoprotein, and does not bind to the p80 form of the tumor necrosis factor receptor. Also provided is an isolated and purified protein kinase that binds to the cytoplasmic domain of the p60 form of the tumor necrosis factor receptor, said kinase phosphoryllates the p60 form of the tumor necrosis factor receptor. Also provided are various methods of manipulating this tumor necrosis factor receptor-associated protein and kinase in order to reduce various biological effects of tumor necrosis factor. |
| 5,854,275 | Dec. 29, 1998 | Cyclic imide derivatives | The invention relates to a compound of the formula I [See Original Patent for Chemical Structure Diagram] I wherein R<1> is a cyclic imide group and X, Y, R<2>, and R<3> are as defined herein. The invention further relates to pharmaceutical compositions containing, and methods of using, compounds of the formula I. Compounds of the formula I are useful in the treatment of diseases related to the production of matrix metalloproteinases and tumor necrosis factor. |
| 5,854,271 | Dec. 29, 1998 | Effective method for the amelioration and prevention of tissue and cellular damage | The administration of histidine is able to prevent and ameliorate tissue and cellular damage which is caused by damaging levels of cytokines and growth factors. It is shown that histidine, when administered in therapeutic quantities is able to inhibit cytokines and growth factors involved in cell and tissue damage. In addition, the method of administering histidine to inhibit these molecules can prevent and ameliorate tissue, vessel and cell damage from restenosis, burns, surgical procedures and other disorders which cause and result from damaged tissues, vessels and cells. |
| 5,854,257 | Dec 29, 1998 | Naphthyridinone derivatives | Compounds of formula I [See Original Patent for Chemical Structure Diagram] I including pharmaceutically acceptable salts thereof in which R1 represents a phenyl C[1–6] alkyl group (in which the phenyl ring is optionally substituted by one or more of the following: halo, a C[1–4]alkyl group, a C[1–4]alkoxy group, hydroxy or trifluoromethyl) and the alkyl chain is optionally substituted by one or more C[1–2]alkyl groups; R2 represents a C[2–6]alkoxycarbonyl group; and R3 represents hydrogen or halo are disclosed, which are antirheumatic agents and are useful as modulators of cytokine synthesis, immunomodulatory agents, antiinflammatory agents and anti-allergic agents. Compositions containing these compounds and processes to make these compounds are also disclosed. |
| 5,854,028 | Dec. 29, 1998 | Compositions comprising IL-11 and methods of making and using IL-11 | A novel mammalian cytokine, IL-11, and processes for producing it are disclosed. IL-11 may be used in pharmaceutical preparations for stimulating and/or enhancing cells involved in the immune response and cells involved in the proper functioning of the hematopoietic system. |
| 5,853,977 | Dec. 29, 1998 | Mammalian TNF- alpha convertases | The present invention provides isolated human and bovine TNF- alpha convertases, nucleic acids and recombinant vectors encoding the same, host cells comprising the nucleic acids and vectors, and methods for making the convertases using the host cells. This invention further provides antibodies and antigen binding fragments thereof which speciflcally bind to the convertases and are useful for treating medical conditions caused or mediated by TNF- alpha. Also provided are screening methods for identifying specific inhibitors of mammalian TNF- alpha convertases, and for identifying nucleic acids encoding such convertases. |
| 5,853,623 | Dec. 29, 1998 | Peptidyl compounds and their therapeutic use as inhibitors of metalloproteinases | The present invention concerns novel mercaptoalkylpeptidyl compounds of formula (I) which are useful inhibitors of matrix metalloproteinase and/or TNF-mediated diseases including degenerative diseases and certain cancers. The invention also concerns methods of treating patients suffering from disorders or diseases which can be attributed to or are associated with matrix metalloproteinase or TNF activity. |
| 5,852,173 | Dec. 22, 1998 | TNF receptor death ligand proteins and inhibitors of ligand binding | Novel TNF receptor death domain ("TNF-R1-DD") ligand proteins are disclosed. Polynucteotides encoding the TNF-R1-DD ligand protein are also disclosed, along with vectors, host cells, and methods of making the TNF-R1-DD ligand protein. Pharmaceuticat compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed |
| 5,851,822 | Dec. 22, 1998 | Inflammation-induced expression of a recombinant gene | The present invention describes methods of controlling and regulating the inflammatory reaction generated in response to various toxins, immunogens, pathogens and autoimmune insults. The method employs a vector that includes an anti-cytokine protein or antibacterial protein gene under the control of a cytokine responsive promoter. In animal models, adenoviral vectors successfully delivered the vectors to hepatic cells and were subsequently shown to respond only to stimulation by induced cytokines. |
| 5,851,556 | Dec. 22, 1998 | Use of a salt of an alkaline-earth metal as TNF-A or substance P inhibitor in a topical composition and composition obtained | The invention relates to the use of a salt of an alkaline-earth metal in a cosmetic, pharmaceutical, veterinary and/or dermatological composition for treating, in particular, sensitive skins. It relates, in addition, to the use of a salt of an alkaline-earth metal for preventing and/or combating rosacea and/or skin irritation and/or dartre and/or pudic erythema and/or dysesthetic sensation and/or sensation of inflammation and/or pruritus of the skin and/or of the mucous membranes. The salt is in particular strontium nitrate or chloride. |
| 5,849,501 | Dec. 15, 1998 | TNF receptor death domain ligand proteins and method to identify inhibitors of ligand binding | Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory |

TABLE 2-continued

Exemplary Anti-Cytokine Compounds

| Patent No. | Issue Date | Title | Abstract |
|---|---|---|---|
| | | | conditions, and methods of inhibiting TNF-R death domain binding are also disclosed. Methods of identifying inhibitors of TNF-R death domain binding and inhibitors identified by such methods are also disclosed. |
| 5,847,123 | Dec. 8, 1998 | Imide derivatives for inhibiting the production of interleukin-1 beta and the production of tumor necrosis factor alpha | Imide compounds having a propioloyl group or pharmaceutically acceptable salts thereof which exhibit potent activities to inhibit the production of Interleukin 1-beta and also the production of Tumor Necrosis Factor alpha. These imide compounds are useful as a prophylactic or therapeutic agent for inhibiting the production of interleukin 1-beta and the production of Tumor Necrosis Factor alpha, typically for such diseases as chronic rheumatism, sepsis, ulcerative colitis, Crohn's disease and many other related diseases in which interleukin 1-beta and/or Tumor Necrosis Factor alpha would participate. |
| 5,847,099 | Dec. 8, 1998 | TNF receptor death domain ligand proteins | Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed. |
| 5,846,763 | Dec. 8, 1998 | DNA encoding tumor necrosis factor stimulated gene 6 (TSG-6) | TSG-6 protein and functional derivatives thereof, DNA coding therefor, expression vehicles, such as a plasmids, and host cells transformed or transfected with the DNA molecule, and methods for producing the protein and the DNA are provided, as well as antibodies specific for the TSG-6 protein; a method for detecting the presence of TSG-6 protein in a biological sample; a method for detecting the presence of nucleic acid encoding a normal or mutant TSG-6 protein; a method for measuring induction of expression of TSG-6 in a cell using either nucleic acid hybridization or immunoassay; a method for identifying a compound capable of inducing the expression of TSG-6 in a cell; and a method for measuring the ability of a cell to respond to TNF. |
| 5,846,755 | Dec. 8, 1998 | Method for determining the therapeutic activity of metalloproteinase inhibitor compounds | A method for determining the therapeutic potential of peptidomimetic compounds as inhibitors of zinc-dependent metalloproteinase activity associated with pathological conditions of humans and animals. |
| 5,843,943 | Dec. 1, 1998 | Compounds for inhibition of ceramide-mediated signal transduction | Novel, heterocyclic compounds having at least one ring nitrogen, disclosed side chains and, in some embodiments, an oxygen ortho to the ring nitrogen inhibit inflammatory responses associated with TNF- alpha and fibroblast proliferation in vivo and in vitro. The compounds of the invention neither appreciably inhibit the activity of cAMP phosphodiesterase nor the hydrolysis of phosphatidic acid, and are neither cytotoxic nor cytostatic. Preferred compounds of the invention are esters. Methods for the use of the novel compounds to inhibit ceramide-mediated intracellular responses to stimuli in vivo (particularly TNF- alpha ) are also described. The methods are expected to be of use in reducing inflammatory responses (for example, after angioplasty), in limiting fibrosis (for example, of the liver in cirrhosis), in inhibiting cell senescence, cell apoptosis and UV induced cutaneous immune suppression. |
| 5,843,918 | Dec. 1, 1998 | Anti-endotoxin compounds | Disdosed are lipid A analogs useful for the treatment of septic shock and LPS-mediated activation of viral infection. |
| 5,843,791 | Dec. 1, 1998 | TNF receptors, TNF binding proteins and DNAs coding for them | DNA sequences adding for a TNF-binding protein and for the TNF receptor of which this protein constitutes the soluble domain. The DNA sequences can be used for preparing recombinant DNA molecules in order to produce TNF-binding protein and TNF receptor. With the aid of the TNF receptor or fragments thereof or with the aid of suitable host organisms transformed with recombinant DNA molecules containing the DNA which codes for the TNF receptor or fragments or modifications thereof, it is possible to investigate substances for their interaction with the TNF receptor and/or for their effect on the biological activity of TNF. |
| 5,843,693 | Dec. 1, 1998 | Assay method for screening for inhibitors of proTNF conversion | Methods and materials are disclosed for the production of purified, active recombinant human neutrophil protease, PR-3, via activation of a pro-form herein referred to as proPR-3. Human PR 3 is useful for discovering inhibitors of excessive release of mature, active TNF alpha. Also disclosed are methods for the identification of inhibitors of the conversion of the pro-form of TNF alpha to its mature active form. |
| 5,843,678 | Dec 1, 1998 | Osteoprotegerin binding proteins | A novel polypeptide, osteoprotegerin binding protein, involved in osteolcast maturation has been identified based upon its affinity for osteoprotegerin. Nucleic acid sequences encoding the polypeptide, or a fragment, analog or derivative thereof, vectors and host cells for production, methods of preparing osteoprotegerin binding protein, and binding assays are also described. Compositions and methods for the treatment of bone diseases such as osteoporosis, bone loss due to arthritis or metastasis, hypercalcemia, and Paget's disease are also provided. |
| 5,843,675 | Dec. 1, 1998 | TNF receptor death domain ligand proteins and inhibitors of ligand binding | Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed. |
| 5,843,452 | Dec. 1, 1998 | Immunotherapy composition and method | A composition for use in immunosuppression therapy is disclosed. The composition includes an immunosuppressant drug, such as cyclosporin A, and an ethanol extract of the root xylem of *Tripterygium wilfordii*. The extract is effective alone, or in combination with such an immunosuppressant, in the treatment of transplantation rejection. Also disclosed is |

TABLE 2-continued

Exemplary Anti-Cytokine Compounds

| Patent No. | Issue Date | Title | Abstract |
|---|---|---|---|
| | | | a method of immunosuppression that includes administering to a subject a pharmaceutically effective amount of an immunosuppressant drug and an extract of the type above, in an amount effective to potentiate the action of the drug. |
| 5,840,724 | Nov. 24, 1998 | Compounds containing phenyl linked to aryl or heteroaryl by an aliphatic- or heteroatom-containing linking group | This invention is directed to the pharmaceutical use of phenyl compounds, which are linked to an aryl moiety by various linkages, for inhibiting tumor necrosis factor. The invention is also directed to the compounds, their preparation and pharmaceutica( compositions containing these compounds. Furthermore, this invention is directed to the pharmaceutical use of the compounds for inhibiting cyclic AMP phosphodiesterase. |
| 5,840,277 | Nov. 24, 1998 | Treatment of chronic pulmonary inflammation | A method and medicant for the inhibition of activation of the nuclear transcription NF-kappa B comprising administering an effective amount of a compound of the formula: [See Original Patent for Chemical Structure Diagram] where R = ethylene, R' = C4 to C14 straight chain or branched alkyl, x is greater than 1, and y = 8 to 18 is provided. The medicant is preferably administered by aerosolization into the mammalian respiratory system. The medicant may also be applied to the mammalian skin. Preferably the medicant includes a physiologically acceptable carrier which may be selected from buffered saline isotonic saline, normal saline petroleum-based ointments and U.S.P. cold cream. There is further provided a method wherein said medicant includes an anti-inflammatory steroid. In addition a method and medicant for treating cutaneous inflammatory disorders, inhibiting the secretion of the pro-inflammatory cytokines TNF, IL-1, IL6, IL-8 and the growth factor GM-CSF is provided. |
| 5,837,719 | Nov. 17, 1998 | 2,5-substituted aryl pyrroles, compositions containing such compounds and methods of use | The present invention addresses 2,5-substituted aryl pyrroles of the formula: [See Original Patent for Chemical Structure Diagram] or a pharmaceutically acceptable salts thereof, as well as compositions containing such compounds and methods of treatment. The compounds are useful for treating Cytokine mediated diseases, which refers to diseases or conditions in which excessive or unregulated production or activity of one or more cytokines occurs. Interleukin-1 (IL-1), Interleukin-6 (IL-6), Interleukin-8 (IL-8) and Tumor Necrosis Factor (TNF) are cytokines which are involved in immunoregulation and other physiological conditions, such as inflammation. The compounds also have glucagon antagonist activity. |
| 5,837,293 | Nov. 17, 1998 | Use of interleukin-10 analogs for antagonists to treat endotoxin- or superantigen-induced toxicity | A method is provided for reducing an inflammatory response in a mammal comprising administering to a mammal at risk of developing or afflicted with an inflammatory response characterized by substantially elevated levels of IL-1 alpha, IL-1 beta, IL-6, IL-8 and TNF alpha, an amount of IL-10 effective to substantially lower the levels of such cytokines. |
| 5,837,342 | Nov. 17, 1998 | Use of an interleukin-10 antagonist to treat a B cell mediated autoimmune disorder | A method is provided for toting a B cell mediated autoimmune disorder comprising administering an effective amount of an interleukin-10 antagonist. |
| 5,837,340 | Nov. 17, 1998 | Methods of treating allergies with M-CSF | This invention provides medical uses of a M-CSF, particularly a method and composition for treating inflammatory disease and allergy using natural M-CSF or recombinant M-CSF or the derivatives thereof. |
| 5,834,435 | Nov. 10, 1998 | Inhibition of TNF- alpha pleiotropic and cytotoxic effects | The pleiotropic effects of TNF alfa in a wide variety of mammalian cell types is decreased and treated by administering glucosaminylmuramyl peptides with D-amino acid residue in a second or third position from the proximal end. New methods for nonspecific oral, vaginal, and topic inhibition is proposed. Inhibition of cytotoxicity of TNF alfa is also achieved. |
| 5,834,419 | Nov. 10, 1998 | Chemokine binding protein and methods of use therefor | The present invention provides a method of use for a novel type chemokine binding protein encoded by poxviruses and having amino acid sequence homology wth the myxoma virus T7 interferon- gamma receptor homolog against disease syndromes associated with acute or chronic dysregulated inflammatory responses. |
| 5,833,976 | Nov 10, 1998 | Use of interleukin-10 (IL-10) to treat endotoxin- or superantigen-induced toxicity | A method is provided for treating septic shock or toxic shock that comprises administering an effective amount of interleukin-10. |
| 5,830,994 | Nov. 3, 1998 | Peptide derivatives of alpha-MSH and their application | Provided is a compound containing a peptide of at least 4 amino acids including the following sequence: His Phe* Arg, wherein Phe* represents phenylalanine or a halogenated derivative of phenylalanine the said peptide being conjugated with thioctic acid, dihydrolioic acid, or N-lipoyl-lysine, in the form of the corresponding salts, esters or amides. In particular, compounds with anti-allergic and anti-inflammatory activities on the one had, and melanogenesis-activating activities on the other, are described. |
| 5,830,742 | Nov. 3, 1998 | TNF- alpha converting enzyme | A metalloprotease that converts TNF- alpha from the 26 kD cell form to the 17 kD form has been isolated and purified and the cDNA sequence known. In particular, the protease has a molecular weight of approximately 80 kD. The isolated and purified protease is useful for designing an inhibitor thereof, and may find use as a therapeutic agent. Assays for detecting the protease-inhibiting activity of a molecule are also an aspect of the invention. |
| 5,830,436 | Nov. 3, 1998 | Method of mucociliary clearance in cystic fibrosis patients using alkylaryl polyether alcohol polymers | A method and medicament for the inhibition of oxidants comprising administering a treatment effective amount of alkylaryl polyether alcohol polymers to a chemical or biologic system in need thereof. Also, a method and medicament for mucociliary clearance, inhibition of cytokine production, and inhibition of interleukin-8 production in cystic fibrosis patients. The method involves administering a treatment effective amount of alkylaryl polyether alcohol polymers to a chemical or biologic system in need thereof. The medicament is preferably administered by aerosolization into the mammalian respiratory system. The medicament may also be applied to the mammalian skin. Preferably, the medicament includes a physiologically acceptable carrier which may be selected from the |

TABLE 2-continued

Exemplary Anti-Cytokine Compounds

| Patent No. | Issue Date | Title | Abstract |
|---|---|---|---|
| | | | group consisting of physiologically buffered saline, isotonic saline, normal saline, petrolatum based ointments and U.S.P. cold cream. |
| 5,824,551 | Oct. 20, 1998 | Method for modulating cell apoptosis | The invention is based upon the newly recognized ability of beta chemokines to inhibit cell apoptosis. In particular, apoptosis of T cells is described. The known beta chemokines 309 and TCA-3 are examples of the beta chemokines which inhibit apoptosis. One aspect of the invention is the use of these molecules to inhibit apoptosis. A second aspect of the invention is the use of beta chemokine inhibitors or antagonists to provoke apoptosis. |
| 5,821,366 | Oct. 13, 1998 | Xanthines and their therapeutic use | 1,3-Disubstituted-zanthines have therapeutic utility via TNF or phosphodiesterase inhibition. |
| 5,821,262 | Oct. 13, 1998 | Hydroxamic acid derivatives as inhibitors of cytokine production | A compound of formula (I): [See Original Patent for Chemical Structure Diagram] (I) wherein: R<1> represents a (C1–C6) alkyl, phenyl, substituted phenyl, or heterocyclyl group; R<2> represents a (C1–C6) alkyl group; R3<3> represents: (i) the side chain of arginine, lysine, tryptophan, histidine, serine, threonine, or cysteine, in which any polar amino, hydroxy, mercapto, guanidyl, imidazolyl or indolyl group is rendered substantially non-polar by substitution at the polar N-, O- or S-atom; or (ii) the side chain of aspartic or glutamic acid, in which side chain the carboxylic acid group is amidated; R<4> represents hydrogen or a (C1–C6) alkyl or phenyl (C1–C6) alkyl group; R<5> represents hydrogen or and n is 0, 1 or 2; or substituted phenyl groups; or a salt solvate or hydrate thereof. Compositions containing compound (I) and methods for treatment of diseases or conditions mediated by TNF or MMPs in mammals. |
| 5,820,858 | Oct. 13, 1998 | Methods and compositions for inhibiting CD14 mediated cell activation | This invention provides monoclonal antibodies that bind to the cell surface CD14 receptor and soluble CD14 receptor. The antibodies are useful for the detection of the presence of cell surface and soluble CD14 in a sample. Chimeric and CDR grafted antibodies generated from the above monoclonal antibodies are further provided. Pharmaceutical compositions containing the above biological compositions are provided. These are useful to treat and prevent LPS-associated disorders, such as sepsis. |
| 5,814,661 | Sep. 29, 1998 | Use of Phthalidyliden esters of carnitine and alkanoyl carnitines for the treatment of endotoxic shock | A therapeutical method for treating endotoxic shock which comprises administering to a patient in need thereof a (3-phthalidyliden) alkyl ester of carnitine or alkanoyl carnitine, is disclosed. |
| 5,811,549 | Sep. 22, 1998 | Process of preparing imidazole compounds | Novel 1,4,5-substituted imidazole compounds and compositions for use in therapy as cytokine inhibitors. |
| 5,811,455 | Sep. 22, 1998 | Compounds useful for treating allergic or inflammatory diseases | [See Original Patent for Chemical Strucutre Diagram] (I) [See Original Patent for Chemical Structure Diagram] (II) Novel cyclohexanes of formulas (I) and (II) are described herein. They inhibit the production of Tumor Necrosis Factor and are useful in the treatment of disease states mediated or exacerbated by TNF production; these compounds are also useful in the mediation or inhibition of enzymatic or catalytic activity of phosphodiesterase IV. |
| 5,811,300 | Sep. 22, 1998 | TNF- alpha ribozymes | Enzymatic RNA molecules which cleave TNF- alpha mRNA. |
| 5,811,118 | Sep. 22, 1998 | Methods of treatment using unilamellar liposomal arachidonic acid metabolite formulations | This invention provides a method of adminstering an arachidonic acid metabolite, such as prostaglandin E1, to an animal. The metabolite is given to the animal, typically a human, in asspcoatopm with a unilamellar liposome comprising a lipid and a release-inhibiting aqueous buffer. This method can be used to treat animals afflicted with disorders characterized by cell activation and adhesion, inflammation or toxemia. |
| 5,808,029 | Sep 15, 1998 | DNA encoding a human TNF binding protein | The present invention is concerned with non-soluble proteins and soluble or insoluble fragments thereof, which bind TNF, in homogeneous form, as well as their physiologically compatible salts, especially those proteins having a molecular weight of about 55 or 75 kD (non-reducing SDS-PAGE conditions), a process for the isolation of such proteins, antibodies against such proteins, DNA sequences which code for non-soluble proteins and soluble or non-soluble fragments thereof, which bind TNF, as well as those which code for proteins comprising partly of a soluble fragment, which binds TNF, and partly of all domains except the first of the constant region of the heavy chain of human immunoglobulins and the recombinant proteins coded thereby as well as a process for their manufacture using transformed pro- and eukaryotic host cells. |
| 5,807,884 | Sep. 15, 1998 | Treatment for atherosclerosis and other cardiovascular and inflammatory diseases | A method for the treatment of cardiovascular diseases and noncardiovascular inflammatory diseases that are mediated by VCAM-1isprovided that includes the removal, decrease in the concentration of, or prevention of the formation of oxidized polyunsaturated fatty acids, or interferes with a complex formed between a polyunsaturated fatty acid or an oxidized polyunsaturated fatty acid and a protein or peptide that mediates the expression of VCAM-1. A method is also provided for suppressing the expression of a redox-sensitive gene or activating a gene that is suppressed through a redox-sensitive pathway, that includes administering an effective amount of a substance that prevents the oxidation of the oxidized signal, and typically, the oxidation of a polyunsaturated fatty acid, or interferes with a complex formed between the oxidized signal and a protein or peptide that mediates the expression of the redox gene. |
| 5,804,588 | Sep. 8, 1998 | Quinoline carboxanides and their therapeutic use | The subject invention concerns novel compounds of the general formula (I) [See Original Patent for Chemical Structure Diagram] that are useful in treating disease states, such as those states associated with proteins that mediate cellular activity. The compounds of the subject invention can be used, for example, to inhibit tumor necrosis factor and/or phosphodiesterase IV. The subject invention also concerns methods for treating disease states using the compounds of the invention. |

TABLE 2-continued

Exemplary Anti-Cytokine Compounds

| Patent No. | Issue Date | Title | Abstract |
|---|---|---|---|
| 5,801,195 | Sep. 1, 1998 | Immunotherapeutic aryl amides | Novel aryl amides are inhibitors of tumor necrosis factor alpha and can be used to combat cachexia, endotoxic shock, and retrovirus replication. A typical embodiment is N-benzoyl-3-amino-3-(3',4'-dimethoxyphenyl)propanamide. |
| 5,798,368 | Aug. 25, 1998 | Tetrasubstituted 2-(2,6-dioxopiperidin-3-yl)-1-oxoisoindolines and method of reducing TNF alpha levels | Tetrasubstituted 1-oxo-2-(2,6-dioxopiperidin-3-yl)isoindolines reduce the levels of TNF alpha in a mammal. A typical embodiment is 1-oxo-2-(2,6-dioxopipendin-3-yl)-4,5,6,7-tetrafluoroisoindoline. |
| 5,795,975 | Aug 18, 1998 | TNF receptor promoter | A DNA molecule containing the endogenous first intron-located p55 TNF-R gene promoter/enhancer sequence is provided. Also provided is a DNA molecule which contains a gene in operative association with a promoter sequence that includes the endogenous first intron-located p55 TNF-R gene promoter/enhancer sequence. |
| 5,795,967 | Aug. 18, 1998 | Tumor necrosis factor antagonists and their use | Tumor necrosis factor antagonists are administered in therapeutically effective doses to suppress inflammatory immune-potentiated events. The antagonists of this invention typically are selected from among several classes but preferably are neutralizing antibodies directed against tumor necrosis factor. The antagonists are useful in suppressing transplantation immunity and in the treatment of autoimmune diseases. |
| 5,795,859 | Aug. 18, 1998 | Peptide which abrogates TNF and/or LPS toxicity | The present invention provides peptides which have the ability to abrogate TNF toxicity and/or LPS toxicity. The present invention further relates to compositions induding these peptides as the active ingredient and methods of anti-inflammatory treatment involving the administration of this composition. The peptides of the present invention are based primarily on residue 1 to 26 of human TNF. |
| 5,789,550 | Aug. 4, 1998 | TRAF inhibitors | The invention concerns novel inhibitors of tumor necrosis factor receptor associated factor-(TRAF) mediated signal transduction. The invention encompasses the novel inhibitor proteins (I-TRAFs), nucleic acid encoding them, methods for their recombinant production, and their use in screening assays and as pharmaceuticals. |
| 5,780,667 | Jul. 14, 1998 | Compounds, compositions and treatment of allergies and inflammation therewith | Novel cyclohexane derivatives of Formula (I) [See Original Patent for Chemical Structure Diagram] are described herein. These compounds inhibit the production of Tumor Necrosis Factor and are useful in the treatment of disease states mediated or exacerbated by TNF production; they are also useful in the mediation or inhibition of enzymatic or catalytic activity of phosphodiesterase IV and are therefore useful in the treatment of disease states in need of mediation or inhibition thereof. |
| 5,777,176 | Jul. 7, 1998 | 4,4-(disubstituted)cyclohexan-1-ol dimers and related compounds | The present invention relates to novel dimers of 4,4-(disubstituted)cyclohexan-1-ol dimers and delated compounds, pharmaceutical compositions containing these compounds, and their use in treating allergic and inflammatory diseases and for inhibiting the production of Tumor Necrosis Factor (TNF). |
| 5,777,160 | Jul. 7, 1998 | 1,4,4-(trisubstituted)cyclohex-1-ene dimers and related compounds | This invention relates to certain 1,4,4-(trisubstituted)cyclohex-1-ene dimers and related compounds which are useful in treating allergic and inflammatory diseases and for inhibiting the production of Tumor Necrosis Factor (TNF). |
| 5,776,954 | Jul. 7, 1998 | Substituted pyridyl pyrroles, compositions containing such compounds and methods of use | The present invention addresses substituted pyridyl pyrroles, as well as compositions containing such compounds and methods of treatment. The compounds in the present invention are glucagon antagonists and inhibitors of the biosynthesis and action of TNF alpha and IL1. The compounds block the action of glucagon at its receptors and thereby decrease the levels of plasma glucose. The instant pyrroles are also inhibitors of TNF alpha and IL1 and may be used as antidiabetic agents as well as other cytokine mediated diseases. Cytokine mediated diseases refers to diseases or conditions in which excessive or unregulated production of one or more cytokines occurs. Interleukin-1 (IL-1) and Tumor Necrosis Factor (TNF) are cytokines produced by a variety of cells, which are involved in immunoregulation and other physiological conditions, such as inflammation. |
| 5,776,947 | Jul. 7, 1998 | Use of quinoline-3-carboxamide compounds for inhibiting the production of tumor necrosis factor (TNF) and/or for the treatment of septic shock | The use of a quinoline-3-carboxamide compound comprising structure (I), optionally with substituents for the hydrogen atoms shown (H<1–9>), and a salt of compound (I) where (a) represents that there are two conjugated double bonds between the atoms comprised by the dashed line, (b) X1 and X2 are separately selected form an oxygen atom or an NH<9> group, said X1 and X2 being bound by a single bond to the ring when attached to H<7> or H<8> and by a double bond when not bound to H<7> or H<8>, (c) H<1–9>; are hydrogens with the provision that H<9> is only present when at least one of X1 and X2 is the NH<9> group, (d) H<7> and H<8> are hydrogens that are attached to different atoms selected among X1, X2 and the nitrogen atom (N) in the quinoline ring, for the manufacture of a composition intended for inhibiting the production of tumor necrosis factor TNF in a living body and/or the treatment of septic shock in a living body. |
| 5,776,915 | Jul. 7, 1998 | Phosphocholines of retinoids | Novel retinoid phosphocholines are disclosed having the general Formula (I): [See Original Patent for Chemical Structure Diagram] wherein R represents a retinyl or retinoyl moiety. The optical and geometric isomers of compounds of Formula (I) and the pharmaceutically-acceptable salts thereof, are also disclosed. The subject compounds exhibit anti-tumor, anti-psoriatic and anti-inflammatory activities in addition to their inherent Vitamin A-like activities. The invention embraces the novel compounds, pharmaceutical compositions thereof, and methods of using the same. |
| 5,773,582 | Jun. 30, 1998 | Tumor necrosis factor muteins | Muteins of human tumor necrosis factor (hTNF), a process for production thereof, and DNAs encoding these muteins are found to have a superior antitumor activity and lower acute lethal toxicity compared to the wild-type human tumor necrosis factor. |
| 5,773,467 | Jun. 30, 1998 | Benzoluran sulphonanmides | Benzoluran carboxides and sulphonamides have therapeutic utility, e.g. in the treatment of inflammation and asthma, by virtue of their ability to inhibit phosphodiesterases and tumor necrosis factor. |

TABLE 2-continued

Exemplary Anti-Cytokine Compounds

| Patent No. | Issue Date | Title | Abstract |
|---|---|---|---|
| 5,772,997 | Jun. 30, 1998 | Monoclonal antibodies directed to the HER2 receptor | A method of inhibiting growth of tumor cells which overexpress a growth factor receptor or growth factor by treatment of the cells with antibodies which inhibit the growth factor receptor function, is disclosed. A method of treatment tumor cells with antibodies which inhibit growth factor receptor function, and with cylotoxic factor(s) such as tumor necrosis factor, is also disclosed. By inhibiting growth factor receptor functions tumor cells are rendered more susceptible to cytotoxic factors. |
| 5,770,694 | Jun. 23, 1998 | Genetically engineered BPI variant proteins | The present invention provides a composition comprising a BPI Protein and an anionic compound which composition exhibits (1) no bactericidal activity and (2) endotoxin neutralizing activity. Also, this invention provides methods for using BPI Proteins. |
| 5,770,624 | Jun. 23, 1998 | Certain alpha-substituted arylsulfonamido acetohydroxamic acids | Particularly the invention relates to the compounds of formula I [See Original Patent for Chemical Structure Diagram](I) wherein Ar represents carbocyclic aryl, heterocyclic aryl or biaryl;<br>R1 represents lower alkyl, cycloalkyl, aryl-lower alkyl, lower alkoxy-lower alkyl, aryl, cycloalkyl-lower alkyl, halo-lower alkyl;<br>R2 represents hydrogen or lower alkyl;<br>R3 and R4 represent independently hydrogen, lower alkyl, lower alkoxy, halo, hydroxy, acyloxy, lower alkoxy-lower alkoxy, trifluoromethyl or cyano; or R3 and R4 together represent lower allylenedioxy;<br>n represents an integer from 1 to 5;<br>pharmaceutically acceptable prodrug derivatives; and pharmaceutically acceptable salts thereof; methods for preparation thereof;<br>pharmaceutical compositions comprising said compounds; and a method of inhibiting TNF-alpha activity and matrix-degrading metalloproteinases in mammals using such compounds. |
| 5,770,402 | Jun. 23, 1998 | DNA encoding macrophage inflammatory protein-1 gamma | Disclosed are novel nucleic acid and peptide compositions comprising a constitutively-expressed CC chemokine. Also disclosed are methods of use for MIP-1 gamma amino acid sequences and the DNA segments which encode them in the stimulation of an immune response, the production of limited pyrexia, the treatment of proliferative cell disorders and T-cell mediated diseases, and the prophylaxis of bacterial sepsis in an animal. |
| 5,770,401 | Jun. 23, 1998 | Methods and compositions for treating allergic reactions | Methods and compositions for treating allergic reactions, including cutaneous, ocular, nasal and Bronchial allergic disease, are disclosed. Interleukin-1 and Tumor Necrosis Factor receptors, and analogues thereof, are employed which bind the respective effector competitively and thereby suppress allergic reactions. |
| 5,770,195 | Jun 23, 1998 | Monoclonal antibodies directed to the her2 receptor | A method of inhibiting growth of tumor cells which overexpress a growth factor receptor or growth factor by treatment of the cetls with antibodies which inhibit the growth factor receptor function, is disclosed A method of treating tumor cells with antibodies which inhibit growth factor receptor function, and with cytotoxic factor(s) such as tumor necrosis factor, is also disclosed. By inhibiting growth factor receptor functions tumor cells are rendered more susceptible to cytotoxic factors. |
| 5,767,151 | Jun. 16, 1998 | 3,3-(disubstituted) cyclohexan-1-ylidine acetate dimers and related compounds | The present invention relates to novel 3,3-(disubstituted)-cyclohexan-1-ylidene acetate dimers of Formula (I): [See Original Patent for Chemical Structure Diagram] I and related compounds, pharmaceutical compositions containing these compounds and their use in treating allergic and inflammateory diseases and for inhibiting the production of Tumor Necrosis Factor (TNF). |
| 5,767,120 | Jun. 16, 1998 | Tricyclic derivatives, compositions and methods of use | Disclosed are compounds of Formula I: [See Original Patent for Chemical Structure Diagram] (I) or a pharmaceutically acceptable salt or solvate thereof, wherein: R<3> is alkyl, alkenyl, alkynyl, aryl, alkaryl, aralkyl, cycloalkyl, acyloxymethyl, alkoxy, alkoxymethyl, or alkyl substituted with cycloalkyl;<br>R<4> is H, alkyl, alkenyl, alkoxy, or —OH.<br>Also disclosed are pharmaceutical compositions containing compounds of Formula methods for inhibiting tumor necrosis factor- alpha and methods for treating septic shock, inflammation, or allergic disease by administering a compound of Formula I. |
| 5,767,097 | Jun. 16, 1998 | Specific modulation of Th1/Th2 cytokine expression by ribavirin in activated T-lymphocytes | Ribavirin is administered to a patient in a dosage range which is effective to modulate tymphokine expression in activated T cells. In particutar, ribavirin is used to suppress Th2-mediated T cell responses and promote Th1-mediated T cell response. Thus, instead of administering ribavirin in its well-recognized role as an anti-viral agent, ribavirin is herein used in the treatment of imbalances in lymphokine expression. Such imbalances may be found to be concomitants of allergic atopic disorders such as allergic asthma and atopic dermatitis, hetminth infection and leishmaniasis, and various primary and secondary immunodeficiencies, which may or may not also be associated with viral infection. |
| 5,766,917 | Jun. 16, 1998 | Method for identifying and producing a protease capable of cleaving the TNF receptor | Molecules which influence the shedding of the cell-bound p55 Tumor Necrosis Factor receptor (p55-TNF-R), are provided, together with methods of producing them. |
| 5,766,865 | Jun. 16, 1998 | Cell lines capable of detecting low levels of cytokines in biological fluids | A method of genetically engineering a cell line capable of detecting bioactive cytokines or growth factors is provided. Cells lines produced by this method and methods of using these cell lines to detect bioactive cytokines or growth factors in a biological fluid are also provided. |
| 5,763,621 | Jun 9, 1998 | Metalloproteinase inhibitors | A compound of formula (I): [See Original Patent for Chemical Structure Diagram] wherein R4 is an optionally substituted C3–C8 cycloalkenyl group. The compounds are inhibitors of matrix metalloproteinases. |
| 5,763,567 | Jun. 9, 1998 | Biologically active peptides from funcional domains of | The present invention provides peptides having an amino acid sequence that is the amino acid sequence of a human bactericidal/permeability-increasing protein (BPI) functional |

TABLE 2-continued

Exemplary Anti-Cytokine Compounds

| Patent No. | Issue Date | Title | Abstract |
|---|---|---|---|
| | | bactericidal/permeability-increasing protein and uses thereof | domain or a subsequence thereof, and variants of the sequence or subsequence thereof, having at least one of the BPI biological activities, such as heparin binding, heparin neutralization, LPS binding, LPS neutralization or bactericidal activity. The invention provides peptides and pharmaceutical compositions of such peptides for a variety of therapeutic uses. |
| 5,763,423 | Jun. 9, 1998 | Pharmaceutical compositions, novel uses, and novel form of tocopherylphosphocholine | alpha-tocopherolphosphocholine and salts thereof have been discovered to possess anti-viral, anti-fungal, anti-inflammatory and PAF-antagonist activities. The compound and salts have also been discovered to be capable of forming liposomes. The present invention thus provides methods of treating viral and fungal infections, inflammatory disorders and pathophysiological conditions due to PAF activity in a mammal by administering to the mammal alpha -tocopherolphosphocholine or a pharmaceutically acceptable salt thereof. The invention also provides pharmaceutical compositions comprising alpha -tocopherolphosphocholine or a pharmaceutically acceptable salt thereof and a pharmaceutically acceptable carrier. Further, the invention provides liposomes which comprise alpha -tocopherolphosphocholine or a salt thereof as a structural component of the liposome bilayer. |
| 5,756,499 | May 26, 1998 | Substituted imidazole compounds | Novel 1,4,5-substituted imidazole compounds and compositions for use in therapy as cytokine inhibitors. |
| 5,753,691 | May 19, 1998 | Agents for inhibiting the production of IL-1 beta and the release of TNF alpha | The pharmaceutical use of 1-cinnamoyl-2-pyrrolidinone derivatives having the activities to inhibit the production of IL-1 beta and the retease of TNF alpha. Those derivatives are useful in the treatment or prophylaxis of the diseases such as chronic rheumatism and sepsis. |
| 5,753,666 | May 19, 1998 | Quinotones and their therapeutic use | 1-Alkyl-substituted-quinotone-3-carboxamides have therapeutic utility via inhibition of Phosphodiesterase IV esterase and/or Tumor Necrosis Factor activity. |
| 5,753,653 | May 19, 1998 | Metalloproteinase inhibitors, pharmaceutical compositions containing them and their pharmaceutical uses | The invention relates to compounds of the formula [See Original Patent for Chemical Structure Diagram] I in which Q is a divalent radical having four ring atoms which together with C* and N form a six-membered ring, each of these four ring atoms being unsubstituted or substituted by a suitable substituent and at least one being a heteroatom selected from O, N and S, with the remainder being carbon atoms; and Ar is an aryl or heteroaryl group. The invention further relates to pharmaceutically acceptable prodrugs and pharmaceutically acceptable salts of these compounds. The invention also relates to methods of inhibiting the activity of metalloproteinases, especially MMPs or TNF alpha by administering a compound of the formula I or a salt or prodrug thereof. The invention further relates to pharmaceutical compositions comprising an effective amount of these compounds, salts, and prodrugs. |
| 5,753,628 | May 19, 1998 | Peptide inhibitors of TNF containing predominantly D-amino acids | Peptides which consist of six to eight, predominately D-amino acids and which bind to tumor necrosis factor-alpha, prevent tumor necrosis factor-alpha from binding to its receptors and inhibit tumor necrosis factor-alpha activity are disclosed. Methods of inhibiting tumor necrosis factor-alpha activity and of treating individuals suffering from tumor necrosis factor-alpha-mediated diseases and disorders are disclosed. |
| 5,747,514 | May 5, 1998 | Metalloproteinase inhibitors | The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumor necrosis factor from cells. |
| 5,747,474 | May 5, 1998 | Immunosuppression by administration of N<6>, N<6>-disubstituted cAMP's, analogues thereof, and related nucleosides | Methods for inducing immunosuppression in animals which need immunosuppressive treatment involving administration to animals of a therapeutically effective amount of the cyclic AMP agent HE-33 or its nucleoside. |
| 5,744,304 | Apr. 28, 1998 | Inflammation-induced expression of a recombinant gene | The present invention describes methods of controlling and regulating the inflammatory reaction generated in response to various toxins, immunogens, pathogens and autoimmune insults. The method employs a vector that includes an anti-cytokine protein or antibacterial protein gene under the control of a cytokine responsive promoter. In animal models, adenoviral vectors successfully delivered the vectors to hepatic cells and were subsequently shown to respond only to stimulation by induced cytokines. |
| 5,741,667 | Apr. 21, 1998 | Tumor necrosis factor receptor-associated factors | The invention concerns new tumor necrosis factor receptor associated factors, designated TRAFs. The new factors are capable of specific association with the intracellular domain of the type 2 TNF receptor (TNF-R2) and CD40, and are involved in the mediation of TNF and CD40 ligand biological activities. |
| 5,741,488 | Apr. 21, 1998 | Treatment of rheumatoid arthritis with anti-CD4 antibodies in conjunction with anti-TNF antibodies | A method for treating autoimmune or inflammatory diseases, through the administration of anti-CD4 antibody in conjunction with or sequentially to anti-TNF antibody, is disclosed. The method can be used to aid in therapy for humans and other mammals with a wide variety of autoimmune or inflammatory diseases. |
| 5,739,143 | Apr. 14, 1998 | Imidazole compounds and compositions | Novel 1,4,5-substituted imidazole compounds and compositions for use in therapy as cytokine inhibitors. |
| 5,736,570 | Apr. 7, 1998 | Immunotherapeutic aryl amides | Novel aryl amides are inhibitors of tumor necrosis factor alpha and can be used to combat cachexia, endotoxic shock, and retrovirus replication A typical embodiment is N-benzoyl-3-amino-3-(3',4'-dimethoxyphenyl)propanamide. |
| 5,736,138 | Apr. 7, 1998 | Monoclonal antibodies with specific binding against membrane proteins on human cells, and pharmaceutical | A monoclonal antibody, or fragments thereof, against human TNF receptor protein which antibody neutralizes the known actions of TNF alpha and/or TNF beta is disclosed. The antibody may be chimeric or humanized. Furthermore, the present invention provides a process for obtaining the above monoclonal antibody, as wetl as a pharmaceutical composition containing the above monoclonal antibody and/or the above protein with |

TABLE 2-continued

Exemplary Anti-Cytokine Compounds

| Patent No. | Issue Date | Title | Abstract |
|---|---|---|---|
| | | compositions containing them | antibody properties. |
| 5,731,343 | Mar. 24, 1998 | Method of use of radicicol for treatment of immunopathological disorders | The present invention provides a method of treating an immunopathological disorder having an etiology associated with production of a proinflammatory agent, by administering a compound of the formula: [See Original Patent for Chemical Structure Diagram] where R1 and R2 are independentty H or —COR3; R3 is H, 1–50C alkyl, 1–20C alkoxy, 2–30C alkenyl, 2–30C alkenyloxy, 2–10 alkynyl, 6–14C aryl or aryloxy, a 5–6 membered heterocycte (containing 1–3 N, O and/or S heteroatoms and optionally fused to an aryl group), 3–8C cycloalkyl (optionally fused to aryl) or 5–8C cycloalkenyl; and R4 is a halogen. Examples of such proinflammatory agents include interteukin-1(IL-1), interteukin-6 (IL-6), interferon-gamma (IFN- gamma ), tumor necrosis factor- alpha (TNF- alpha), granutocyle macrophage-colony stimulating factor (GM-CSF), the growth related gene KC, cyclooxygenase-1(COX-1), cyclooxygenase-2 (COX-2), macrophage chemotactic protein (MCP), inducible nitric oxide synthetase (iNOS), macrophage inflammatory protein (MIP), tissue factor (TF), phosphotyrosine phosphatase (PTPase), and endotoxin. |
| 5,730,975 | Mar. 24, 1998 | Treatment of insulin resistance in obesity linked type II diabetes using antagonist to TNF-alpha function | An induction of TNF- alpha mRNA expression has been observed in adipose tissue from four different insulin resistant rodent models of obesity and diabetes. TNF- alpha protein was also elevated locally and systemically. Neutralization of TNF- alpha in obese fa/fa rats caused a significant increase in the peripheral uptake of glucose in response to insulin. A method of treating an animal suffering from insulin resistance in obesity linked Type II diabetes mellitus is disclosed. The method includes providing a therapeutic agent that includes an antagonist to TNF- alpha function in a pharmaceutically acceptable carrier substance and administering a pharmacologically effective amount of the therapeutic agent to the animal. |
| 5,728,845 | Mar. 17, 1998 | Immunotherapeutic nitrites | Novel nitrites are inhibitors of tumor necrosis factor alpha and phosphodiesterase and can be used to combat cachexia, endotoxic shock, retrovirus replication, asthma, and inflammatory conditions. A typical embodiment is 3-Phthalimido-3-(3,4-dimethoxyphenyl)propionitrile. |
| 5,728,844 | Mar. 17, 1998 | Immunotherapeutic agents | Novel amides are inhibitors of TNF alpha and phosphodiesterase and can be used to combat cachexia, endotoxic shock, retrovirus replication, asthma, and inflammatory conditions. A typical embodiment is 3-phthalimido-3-(3-cyclopentyloxy-4-methoxyphenyl)propionamide. |
| 5,728,712 | Mar. 17, 1998 | 3,4-disubstituted-phenylsulphonamides and their therapeutic use | 3,4-Disubstituted-phenylsulphonamides have therapeutic utility via TNF or phosphodiesterase inhibition. |
| 5,726,166 | Mar. 10, 1998 | Malaria treatments | A method of treating or preventing clinical manifestations associated with diseases caused by infectious organisms which express antigens which in the patient stimulate secretion of harmful levels of at least one cytokine, other than diseases caused by organisms which stimulate secretion of cytokines only by expression of lipopolysaccharide, which method comprises administering to a human in need thereof an effective non-toxic amount of a material selected from the group consisting of inhibitors and immunogens wherein said inhibitors are pharmacologically acceptable materials which, in vitro, reduce or abolish secretion, by at least one of human monocytes and mouse peritoneal macrophages, of tumour necrosis factor following stimulation with a phospholipid-containing; tumour necrosis factor-inducing antigen other than lipopolysaccharide, and wherein said immunogens are pharmacologically acceptable materials comprising at least one B-cell epitope and which stimulate production of antibodies which, in vitro, reduce or abolish secretion, by at least one of human monocytes and mouse peritoneal macrophages, of tumour necrosis factor following stimulation with a phospoiipid-containing, tumour necrosis factor-inducing antigen other than lipopolysaccharide. Examples of inhibitors include inositol monophosphate and phosphatidyl inositol lipids. Immunogens include these inhibitors optionally with carrier proteins. |
| 5,725,856 | Mar. 10, 1998 | Monoclonal antibodies directed to the HER2 receptor | A method of inhibiting growth of tumor cells which overexpress a growth factor receptor or growth factor by treatment of the cells with antibodies which inhibit the growth factor receptor function, is disclosed. A method of treating tumor cells with antibodies which inhibit growth factor receptor function, and with cytotoxic factor(s) such as tumor necrosis factor, is also disclosed. By inhibiting growth factor receptor functions tumor cells are rendered more susceptible to cytotoxic factors. |
| 5,723,681 | Mar. 3, 1998 | 3,3-(disubstituted)cyclohexan-1-01 dimers and related compounds | The present invention relates to novel 3,3-(disubstituted)cyclohexan-1-ol dimers and related compounds, pharmaceutical compositions containing these compounds, and their use in treating allergic and inflammatory diseases and for inhibiting the production of Tumor Necrosis Factor (TNF). |
| 5,723,116 | Mar. 3, 1998 | Decreased mortality of severe acute pancreatitis following proximal cytokine blockade | A method for treating acute pancreatitis is disclosed. The method comprises administering to a patient with acute pancreatitis an effective amount of a suitable tumor necrosis factor (TNF) antagonist such as a TNF soluble receptor or a pharmaceutically acceptable salt thereof. |
| 5,721,121 | Feb. 24, 1998 | Mammalian cell culture process for producing a tumor necrosis factor receptor immunoglobulin chimeric protein | The present invention relates to novel process for the preparation of glycoproteins by mammalian cell culture wherein the sialic acid content of the glycoprotein produced is controlled over a broad range of values by manipulating the cell culture environment. The invention provides for processes in which the sialic acid content of the glycoprotein is modified by changes in cell culture parameters which affect cell specific productivity. Preferred embodiments of the invention include cell culture processes in the osmolality of the cell culture is controlled as well as the concentration of a transcription enhancer during the production phase of the cell culture. The invention further provides for novel |

TABLE 2-continued

Exemplary Anti-Cytokine Compounds

| Patent No. | Issue Date | Title | Abstract |
| --- | --- | --- | --- |
| | | | preparations of soluble type 1 tumor necrosis factor immunoglobulin G1 and their uses in the treatment of inflammatory or immune related disorders. |
| 5,720,954 | Feb. 24, 1998 | Monoclonal antibodies directed to the HER2 receptor | A method of inhibiting growth of tumor cells which overexpress a growth factor receptor or growth factor by treatment of the cells with antibodies which inhibit the growth factor receptor function, is disclosed. A method of treating tumor cells with antibodies which inhibit growth factor receptor function, and with cytotoxic factor(s) such as tumor necrosis factor, is also disclosed. By inhibiting growth factor receptor functions tumor cells are rendered more susceptible to cytotoxic factors. |
| 5,720,937 | Feb. 24, 1998 | In vivo tumor detection assay | In vivo assay methods for detecting tumors having amplified expression of the HER2 receptor are disclosed. In the assay, cells within the body of a mammal are exposed to an antibody which specifically binds to the extracellular domain of the HER2 receptor and inhibits growth in vitro of SK-BR-3 breast tumor cells which overexpress p185<HER2> The antibody is generally tagged with a radioactive isotope to permit the extent of binding of the antibody to the cells to be quantified. |
| 5,719,184 | Feb. 17, 1998 | 3,3-(disubstituted)cyclohexan-1-carboxylate dimers and related compounds | The present invention relates to novel 3,3-(disubstituted)cyclohexan-1-carboxylate dimers and related compounds, pharmaceutical compositions containing these compounds, and their use in treating allergic and inflammatory diseases and for inhibiting the production of Tumor Necrosis Factor (TNF). |
| 5,716,981 | Feb. 10, 1998 | Anti-anglogenic compositions and methods of use | The present invention provides compositions comprising an anti-anglogenic factor, and a polymeric carrier. Representative examples of anti-anglogenic factors include Anti-Invasive Factor, Retinoic acids and derivatives thereof, and paclitaxel. Also provided are methods for embolizing blood vessels, and eliminating biliary, urethral, esophageal, and tracheal/bronchial obstructions. |
| 5,716,972 | Feb 10, 1998 | Pyridyl substituted imidazoles | The novel compounds of Formula (I) have been found to be useful cytokine suppressive agents and therefore useful in the treatment and prophylaxis of disease states mediated thereby. |
| 5,716,955 | Feb. 10, 1998 | Substituted imidazole compounds | Novel 1,4,5-substituted imidazoe compounds and compositions for use in therapy as cytokine inhibitors. |
| 5,714,147 | Feb. 3, 1998 | Hybrid immunoglobulins | Novel polypeptides are provided, together with methods for making and using them, and nucleic acids encoding them. These polypeptides are useful as cell surface adhesion molecules and ligands, and are useful in therapeutic or diagnostic compositions and methods. |
| 5,714,140 | Feb. 3, 1998 | Method for inhibiting the production of bioactive IL-1 by administering M-CSF | This invention provides medical uses of a M-CSF, particularly a method and composition for treating inflammatory disease and allergy using natural M-CSF or recombinant M-CSF or the derivatives thereof. |
| 5,712,381 | Jan. 27, 1998 | MADD, a TNF receptor death domain ligand protein | Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed. |
| 5,712,286 | Jan. 27, 1998 | Naphthyridine derivatives | Compounds of formula (I) including pharmaceutically acceptable salts thereof in which R1 represents a C1–6 akyl group; R2 represents a group of the formula COOR4 in which R4 represents a C1–5 akyl group; and R3 represents a group of formula COOR5 in which R5 represents a C1-5 alkyl group are disclosed, which are anti-rheumatic agents and are useful as modulators of cytokine synthesis, immunomodulatory agents, anti-inflammatory agents and anti-allergic agents. Compositions containing these compounds and processes to make these compounds are also disclosed. |
| 5,712,155 | Jan. 27, 1998 | DNA encoding tumor necrosis factor- alpha and -beta receptors | Tumor necrosis factor receptor DNAs and expression vectors encoding TNF receptors, and processes for producing TNF receptors as products of recombinant cell culture, are disclosed. |
| 5,708,142 | Jan. 13, 1998 | Tumor necrosis factor receptor-associated factors | The invention concerns new tumor necrosis factor receptor associated factors, designated TRAF. The new factors are capable of specific association with the intracellular domain of the type 2 TNF receptor (TNF-R2), and are involved in the mediation of TNF biological activities |
| 5,705,389 | Jan 6, 1998 | Oligonucleotides that inhibit production of alpha -tumor necrosis factor | A sequence of anti-direction, anti-messenger RNA oligonucleotides of alpha -TNF characterized in that it possesses the structure of the formula [See Original Patent for Chemical Structure Diagram] I wherein X is hydrogen, or a sequence of 1 to 17 oligonucleotides in free form, in alkylated form, in sulfurated form or in the form of a poly L-lysine derivative useful for stopping the production of alpha -TNF. |
| 5,705,364 | Jan. 6, 1998 | Mammalian cell culture process | The present invention relates to novel process for the preparation of glycoproteins by mammalian cell culture wherein the sialic acid content of the glycoprotein produced is controlled over a broad range of values by manipulating the cell culture environment. The invention provides for processes in which the sialic acid content of the glycoprotein is modified by changes in cell culture parameters which affect cell specific productivity. Preferred embodiments of the invention include cell culture processes in the osmolality of the cell culture is controlled as well as the concentration of a transcription enhancer during the production phase of the cell culture. The invention further provides for novel preparations of soluble type 1tumor necrosis factor immunoglobulin G1and their uses in the treatment of inflammatory or immune related disorders. |

TABLE 2-continued

Exemplary Anti-Cytokine Compounds

| Patent No. | Issue Date | Title | Abstract |
|---|---|---|---|
| 5,703,098 | Dec. 30, 1997 | Immunotherapeutic imideslamides | Imide/amide ethers and alcohols are inhibitors of cytokines including tumor necrosis factor alpha and can be used to combat cachexia, endotoxic shock, arthritis, asthma, and retrovirus replication. A typical embodiment is 3-Phthalimido-3-(3', 4'-dimethoxyphenyl)propan-1-ol. |
| 5,703,092 | Dec. 30, 1997 | Hydroxamic acid compounds as metalloprotease and TNF inhibitors | The present invention provides novel hydroxamic acids and carbocyclic acids and derivatives thereof and to pharmaceutical compositions and methods of use of these novel compounds for the inhibition of matrixmetalloproteinases, such as stromelysin and other matrix metalloproteinases, and also inhibit the production of tumor necrosis factor (TNF), and are therefore useful for the treatment of arthritis and other related inflammatory diseases. These novel compounds are represented by Formula betow: [See Original Patent for Chemical Structure Diagram] Formula I |
| 5,703,038 | Dec. 30, 1997 | Therapeutic uses of bactericidal-permeability-increasing protein dimer products | Improved therapeutic uses of bactericidal/permeability-increasing protein (BPI) involve use of BPI protein product formulations in the form of physiologically stable dimeric associations of BPI protein product monomers characterized by enhanced in vivo biological activity. Preferred formulations include 50 percent or more by weight dimeric product. |
| 5,702,705 | Dec. 30, 1997 | Antibody methods for the treatment of a hormone-mediated disease | Cleavage site blocking antibody that binds to prohormones, preferable Tumor Necrosis Factor, thereby preventing the formation of prohormone fragment(s) by proteolysis of the prohormone, and uses of the antibody including prophylactic and therapeutic methods to treat disease, and diagnostic assays for determining the amount of the prohormone and prohormone fragments present in a patients body. |
| 5,700,909 | Dec 23, 1997 | Prosaposin and cytokine-derived peptides | Prosaposin and peptide derivatives derived therefrom will promote neurite outgrowth in vitro. A peptide consensus sequence was determined by comparing the active neurite outgrowth-inducing saposin C peptide sequence with that of various hematopoietic and neuropoietic cytokines. These cytokine-derived peptides will promote the same processes as their corresponding cytokines. In addition, prosaposin and saposin C promote increased nerve cell myelination ex vivo. |
| 5,700,788 | Dec. 23, 1997 | Ureido derivatives of naphthalenephosphonic acids | Subject of the present invention are new ureido derivatives of naphthalenephosphonic acids having the following formula (I) [See Original Patent for Chemical Structure Diagram] (I) [See Original Patent for Chemical Structure Diagram] wherein each of m and n, which are the same, is an integer of 1 to 4; each of p and q, which are the same, is an integer of 1 gto 3; and each of the R groups, which are the same, is a free or esterified phosphonic acid group; and the pharmaceutically acceptable salts thereof. |
| 5,698,711 | Dec. 16, 1997 | Compounds containing phenyl linked to aryl or heteroaryl by an aliphatic- or heteroatom-containing linking group | This invention is directed to the pharmaceutical use of phenyl compounds, which are linked to an aryl moiety by various linkages, for inhibiting tumor necrosis factor. The invention is also directed to the compounds, their preparation and pharmaceutical compositions containing these compounds. Furthermore, this invention is directed to the pharmaceutical use of the compounds for inhibiting cyclic AMP phosphodiesterase. |
| 5,698,706 | Dec. 16, 1997 | Heterocyclic amides and methods of use | Peptidyl derivatives having a SH or acyl S group and which are amides, primary amides or thioamides, have therapeutic utility via MMP or TNF inhibition. |
| 5,698,579 | Dec. 16, 1997 | Cyclic amides | Cyclic amides are inhibitors of tumor necrosis factor and can be used to combat cachexia, endotoxic shock, and retrovirus replication. A typical embodiment is 3-phenyl-3-(1-oxoisoindolin-2-yl)propionamide. |
| 5,698,564 | Dec. 16, 1997 | Diphenyl disulfide compounds | Diphenyl disulfide compounds having an inhibiting activity against the production of Interleukin-1 beta (IL-1 beta) or the release of Tumor Necrosis Factor alpha (TNF alpha), which are useful in the treatment or prophylaxis of the diseases such as chronic rheumatism and sepsis are described. |
| 5,698,518 | Dec. 16, 1997 | Method for regulating inflammation and tumor growth with calmodulin, calmodulin analogues or calmodulin antagonists | A method of treating patients to inhibit inflammation is disclosed. In the method, an effective amount of calmodulin, a calmodulin analogue or calmodulin receptor agonist is administered to a patient to inhibit production of tumor necrosis factor and/or augment elastase. In another method, an effective amount of calmodulin antagonist is administered to a patient to stimulate immune response or inhibit elastase release. In another embodiment, a diagnostic test is disclosed to be used on patient blood samples to determine individual propensity to regulate tumor necrosis factor and/or elastase by calmodulin, its analogues or receptor agonists. |
| 5,698,391 | Dec 16, 1997 | Methods for synthetic unrandomization of oligomer fragments | Methods useful for the determination of oligomers which have specific activity for a target molecule from a pool of primarily randomly assembled oligomers are provided. The disclosed methods involve repeated syntheses of increasingly simplified sets of oligomers coupled with selection procedures for determining oligomers having the highest activity. Freedom from the use of enzymes allows the application of these methods to any molecules which can be oligomerized in a controlled fashion. |
| 5,698,195 | Dec. 16, 1997 | Methods of treating rheumatoid arthritis using chimeric anti-TNF antibodies | Anti-TNF antibodies, fragments and regions thereof which are specific for human tumor necrosis factor- alpha (TNF alpha ) and are useful in vivo for diagnosis and therapy of a number of TNF alpha -mediated pathologies and conditions, including rheumatoid arthritis as well as polynucleotides coding for murine and chimeric antibodies, methods of producing the antibody, methods of use of the anti-TNF antibody, or fragment, region or derivative thereof, in immunoassays and immunotherapeutic approaches are provided. |
| 5,695,993 | Dec. 9, 1997 | Cloning and regulation of an endothelial cell protein C/activated protein C receptor | Human protein C and activated protein C were shown to bind to endothelium specifically, selectively and saturably (Kd = 30 nM, 7000 sites per cell) in a Ca<2 +> dependent fashion. Expression cloning revealed a 1.3 kb cDNA that coded for a novel type transmembrane glycoprotein capable of binding protein C. This protein appears to be a member of the CD1/MHC superfamily. Like thrombomodulin, the receptor involved in protein C activation, the endothelial cell protein C receptor (EPCR) function and message are both down regulated by exposure of endothelium to TNF. Identification of EPCR as a member of the CD1/MHC superfamily provides insights into the role of protein C in |

TABLE 2-continued

Exemplary Anti-Cytokine Compounds

| Patent No. | Issue Date | Title | Abstract |
|---|---|---|---|
| | | | regulating the inflammatory response, and determination of methods for pharmaceutical use in manipulating the inflammatory response. |
| 5,695,953 | Dec. 9, 1997 | DNA that encodes a tumor necrosis factor inhibitory protein and a recombinant method of production | Tumor Necrosis Factor (TNF) Inhibitory Protein is isolated and substantially purified and the DNA that encodes the TNF inhibitory protein, vectors, host cells, and a recombinant method for producing the encoded protein are also set forth. It has the ability to inhibit: (a) the binding of TNF to its receptors, and (b) the cytotoxic effect of TNF. TNF Inhibitory Protein and salts, functional derivatives and active fractions thereof can be used to antagonize the deleterious effects of TNF. |
| 5,691,382 | Nov. 25, 1997 | Inhibition of TNF production with matrix metaloproteinase inhibitors | The present invention is directed to the method of inhibiting the release of tumor necrosis factor (TNF) in a condition mediated by TNF by administration of certain hydroxamic add derivatives, also known as matrix metalloproteinase inhibitors, and thus the method of this invention is useful in the management of diseases or conditions mediated by TNF. |
| 5,691,381 | Nov. 25, 1997 | Hydroxamic and carbocyclic acids as metalloprotease inhibitors | The present invention provides novel hydroxamic acids and carbocyclic acids and derivatives thereof and to pharmaceutical compositions and methods of use of these novel compounds for the inhibition of matrix metalloproteinases, such as stromelysin, and inhibit the production of tumor necrosis factor alpha, and for the treatment of arthritis and other related inflammatory diseases. these novel compounds are represented by Formula I below [See Original Patent for Chemical Structure Diagram] Formula I |
| 5,688,805 | Nov. 18, 1997 | Tricyclic derivatives, compositions and methods of use | Disclosed are compounds of Formula [See Original Patent for Chemical Structure Diagram] (I) or a pharmaceutically acceptable salt or solvate thereof. Also disclosed are pharmaceutical compositions containing compounds of Formula I, methods for inhibiting tumor necrosis factor- alpha and methods for treating septic shock, inflammation, or allergic disease. |
| 5,686,455 | Nov. 11, 1997 | Imidazole derivatives and their use as cytokine inhibitors | As cytokine inhibitors 2,4,5-triarylimidazole compounds and compositions for use as cytokine inhibitors. |
| 5,686,431 | Nov. 11, 1997 | Methods of using low molecular weight heparins for treatment of pathological processes | The present invention relates to methods for the prevention and/or treatment of pathological processes involving the induction of TNF- alpha secretion comprising a pharmaceutically acceptable carrier and a low molecular Weight heparin (LMWH). In the pharmaceutical compositions of the present invention, the LMWH present in a low effective dose and is administered at intervals of about 5–8 days. Furthermore, the LMWH is capable of inhibiting in vitro TNF- alpha secretion by resting T cells and/or macrophages in response to T cell-specific antigens, mitogens, macrophage activators, disrupted extracellular matrix (dECM), laminin, fibronectin, and the like. |
| 5,686,259 | Nov. 11, 1997 | Assay method for the detection of 26 kd TNF prohormone | Cleavage site blocking antibody that binds to prohormones, preferable Tumor Necrosis Factor, thereby preventing the formation of prohormone fragment(s) by proteolysis of the prohormone, and uses of the antibody including prophylactic and therapeutic methods to treat disease, and diagnostic assays for determining the amount of the prohormone and prohormone fragments present in a patients body. |
| 5,684,222 | Nov. 4, 1997 | Mutant mouse having a disrupted TNFRp55 | The multiple biological activities of tumor necrosis factor (TNF) are mediated by two distinct cell surface receptors of 55 and 75 kDa. Mutant mice of the invention lacking tumor necrosis factor receptor (TNFR) p55 still express functional TNFRp75 molecules at the cell surface. Normal weight and size of the mutant mice are not altered. Thymocyle development and Iymphocyle populations are normal, and clonal deletion of potentially self-reactive T cells is not impaired. Activation of the nuclear transcription factor kappa B (NF- kappa B), however, is completely abrogated after stimulation with TNF. Moreover, TNFRp55 mutant mice are protected from septic shock induced by bacterial endotoxin or superantigen, but Listeria clearance is severely impaired and mutant mice easily succumb to Listeria infection. Thus, the two TNF receptors are not redundant, are independently controlled, and piay different roles in normal and pathological physiology. |
| 5,679,696 | Oct 21, 1997 | Compounds containing phenyl linked to aryl or heteroaryl by an aliphatic-or heteroatom-containing linking group | This invention is directed to the pharmaceutical use of phenyl compounds, which are linked to an aryl moiety by vanous linkages, for inhibiting tumor necrosis factor. The invention is also directed to the compounds, their preparation and pharmaceutical compositions containing these compounds. Furthermore, this invention is directed to the pharmaceutical use of the compounds for inhibiting cyclic AMP phosphodiesterase. |
| 5,679,684 | Oct. 21, 1997 | Hydroxyalkylammonium-pyrimidines and nucleoside derivatives, useful as inhibitors of inflammatory cytokines | Novel hydroxyalkylammonium-pyrimidine of the formula [See Original Patent for Chemical Structure Diagram] (I) and nucieoside derivatives have been found to be useful as inhibitors of inflammatory cytokines. They can be used, inter alia, in the therapy of septic shock, cachexia, rheumatoid arthritis, inflammatory bowel disease, multiple sclerosis and AIDS. The compounds are typically prepared by reaction of an iodo substituted nucleoside with the appropriately substituted hydroxyalkylamine. |
| 5,679,338 | Oct. 21, 1997 | Use of IL-4 for inhibition of the breakdown of articular cartiiage and other tissues | Applicants' invention discloses therapeutic compositions and methods for treating articular cartilage breakdown associated with osteoarthritis and rheumatoid arthritis. The compositions comprise a therapeutically effective amount of IL-4 to reduce or inhibit breakdown of articular cartilage, optionally in the presence of a pharmaceutically acceptable carrier or excipient. Methods for treating articular cartilage breakdown comprise administering a therapeutically effective amount of IL-4 to reduce or inhibit breakdown of articular cartilage, optionally in the presence of a pharmaceutically acceptable carrier to a subject in need of such treatment. The invention also relates to compositions and methods for treating tumor metastases, periodontal disease, emphysema and osteoporosis. |

TABLE 2-continued

Exemplary Anti-Cytokine Compounds

| Patent No. | Issue Date | Title | Abstract |
|---|---|---|---|
| 5,677,182 | Oct. 14, 1997 | Cleavage site blocking antibody to prohormone proteins and uses thereof | Cleavage site blocking antibody that binds to prohormones, preferable Tumor Necrosis Factor, thereby preventing the formation of prohormone fragment(s) by proteolysis of the prohormone, and uses of the antibody including prophylactic and therapeutic methods to treat disease, and diagnostic assays for determining the amount of the prohormone and prohormone fragments present in a patients body. |
| 5,672,347 | Sep. 30, 1997 | Tumor necrosis factor antagonists and their use | Tumor necrosis factor antagonists are administered in therapeutically effective doses to suppress inflammatory immune-potentiated events. The antagonists of this invention typically are selected from among several classes but preferably are neutralizing antibodies directed against tumor necrosis factor. The antagonists are useful in suppressing transplantation immunity and in the treatment of autoimmune diseases. |
| 5,670,527 | Sep. 23, 1997 | Pyridyl imidazole compounds and compositions | Novel 1,4,5-substituted imidazole compounds and compositions for use in therapy as cytokine inhibitors. |
| 5,670,526 | Sep 23, 1997 | 1,3,4-oxadiazoles | 1,3,4-oxadiazole compounds are disdosed. The subject compounds suppress immune function and have hepatoprotection activity. |
| 5,670,506 | Sep 23, 1997 | Halogen, isothiocyanate or azide substituted xanthines | There is disclosed a compound having the formula [See Original Patent for Chemical Structure Diagram] wherein n is an integer from 5 to 9, wherein the core moiety is a heterocylic moiety wherein C[a], C[b], and C[c] are an R or S enantiomer or racemic mixture and the C[a], C[b], and C[c] carbon atoms are bonded together by a single bond, double bond, ether or ester linkages, wherein R1, R2 and R3 are independently halo, hydroxy, hydrogen, keto, isothiocyano, azide or haloacetoxy with the proviso that at least one of R1, R2 or R3 must be a halo, isothiocyano, azide or haloacetoxy group, wherein R4 is hydrogen, C1–6 alkyl, C1–6 alkenyl, cyclo C4–6 alkyl, or phenyl, and wherein halo refers to fluoro, chloro, bromo and iodo and salts thereof and pharmaceutical compositions thereof. |
| 5,670,319 | Sep. 23, 1997 | Assay for tumor necrosis factor receptor-associated factors | The invention concerns new tumor necrosis factor receptor associated factors, designated TRAF. The new factors are capable of specific association with the intracellular domain of the type 2 TNF receptor (TNF-R2), and are involved in the mediation of TNF biological activities. |
| 5,670,149 | Sep. 23, 1997 | Lymphotoxin- beta, Lymphotoxin- beta complexes, pharmaceutical preparations and therapeutic uses thereof | This invention relates to lymphotoxin- beta, a lymphocyle membrane type protein. This protein is found on the surface of a number of cells, including phorbol ester (PNA) stimulated T cell hybridoma II-23.D7 cells. This invention also relates to complexes formed between lymphotoxin- beta and other peptides such as lymphotoxin- alpha and to complexes comprising multiple subunits of lymphotoxin- beta. These proteins and complexes are useful in holding LT- alpha formed within the cell on the cell surface where the LT- alpha /LT- beta complex may act as an inflammation regulating agent, a tumor growth inhibiting agent, a T cell inhibiting agent, a T cell activating agent, an autoimmune disease regulating agent, or an HIV inhibiting agent. Furthermore, the antitumor activity of the LT- alpha /LT- beta complex may be delivered to tumor cells by tumor infiltrating lymphocyles (TILs) transfected with the gene for LT- beta. |
| 5,668,143 | Sep. 16, 1997 | Heterocyclic benzenesulfonylimine derivatives as inhibitors of IL-1 action | The present invention relates to heterocyclic benzenesulfonylimine derivatives and their use as inhibitors of Interleukin-1 (IL-1) action. Such inhibitors are useful in the treatment of various disease states as disclosed herein including rheumatoid arthritis, multiple sclerosis, diabetes mellitus, atherosclerosis, septic shock and pulmonary fibrosis. |
| 5,667,967 | Sep. 16, 1997 | T-cell receptor varible transcripts as disease related markers | Methods are provided for determining relations between autoimmune degenerative diseases and specific variable regions of T-cell receptors as associated with the host HLA or T-cells associated with umbatting neoprofilerative diseases. By identifying the particular T-cell receptors which cause or are the disease in mammals, various prophylactic and therapeutic techniques may be employed for inhibiting the attack of the T-cell receptors on the native protein or tissue enhance the defense. In addition, individuals may be diagnosed as to their propensity for a particular autoimmune disease or the occurrence of such a disease. |
| 5,667,776 | Sep. 16, 1997 | Treatment for biological damage using tumor necrosis factor and a free-radical scavenger | Damage to cells, tissue and other bocly parts in a mammalian host may be treated by using a tumor necrosis factor in conjunction with at least one biological modifier, which may be a free radical scavenger or a metabolic inhibitor. The biological modifier is preferably uric acid, buthionine sulphoximine, vitamin C, aspirin, or nordihydrogualaretic acid. Such a combination may be used to treat, for example, cancer, infectious diseases, and damage caused by radiation therapy, high oxygen tension, and chemotherapy. |
| 5,665,859 | Sep. 9, 1997 | Molecules influencing the shedding of the TNF receptor, their preparation and their use | Molecules which influence the shedding of the cell-bound p55 Tumor Necrosis Factor receptor (p55-TNF-R), are provided, together with methods of producing them. |
| 5,665,777 | Sep. 9, 1997 | Biphenyl hydroxamate inhibitors of matrix metalloproteinases | Compounds of formula [See Original Patent for Chemical Structure Diagram] or a pharmaceutically acceptable salt thereof inhibit matrix metalloproteinases and TNF alpha secretion and are useful in the treatment of inflammatory disease states. Also disclosed are matrix metalloproteinases and TNF alpha secretion inhibiting compositions and a method for inhibiting matrix metalloproteinases and TNF alpha secretion. |
| 5,665,754 | Sep. 9, 1997 | Substituted pyrrolidines | Novel pyrrolidine compounds which are useful for inhibiting the function of Type IV phosphodiesterase (PDE-IV) as well as methods for making the same are disdosed. Applications in treating inflammatory diseases and other diseases involving elevated levels of cytokines, as well as central nervous system (CNS) disorders, are also disclosed. |
| 5,665,714 | Sep. 9, 1997 | N-substituted glycerophosphoethanolamines | The present invention relates to novel, therapeutically active fatty alkyl and alkenyl ether glycerophospholipids bearing a 3-(2-imidazolinyl)-2-imidazolinyl or 2-imidazolinyl substituent on the ethanolamine nitrogen, methods of using the compounds and |

TABLE 2-continued

Exemplary Anti-Cytokine Compounds

| Patent No. | Issue Date | Title | Abstract |
|---|---|---|---|
| | | | pharmaceutically acceptable salts thereof, and pharmaceutical compositions containing same. The novel, therapeutically active compounds and salts of the invention possess anti-tumor, anti-psoriatic, anti-inflammatory, and anti-asthma activities. |
| 5,663,334 | Sep. 2, 1997 | Process for preparing pyrimidyl imidazoles | Novel 1,4,5-substituted imidazole compounds and compositions for use in therapy as cytokine inhibitors. |
| 5,658,949 | Aug. 19, 1997 | Inhibition of tumor necrosis factor by retinoic acid | A novel method of inhibiting production of two important mediators of cellular function, tumor necrosis factor and nitric oxide; and treating a pathophysiological state characterized by an undesirable production or level of tumor necrosis factor or nitric acid. The methods of the present invention employ retinoic acid compounds. The most preferred retinoic acid is all-trans-retinoic acid. Also provided is a method of inhibiting tumor necrosis factor receptors using retinoic acid-like compounds. |
| 5,658,940 | Aug. 19, 1997 | Succinimide and maleimide cytokine inhibitors | Novel succinimides and maleimides are inhibitors of tumor necrosis factor alpha and phosphodiesterase and can be used to combat cachexia, endotoxic shock, retrovirus replication, asthma, and inflammatory conditions. A typical embodiment is methyl 3-(3',4',5',6'-tetrahydrophthalimido)-3-(3",4"-dimethoxyphenyl)propionate. |
| 5,658,903 | Aug. 19, 1997 | Imidazole compounds, compositions and use | Novel 1,4,5-substituted imidazole compounds and compositions for use in therapy as cytokine inhibitors. |
| 5,658,581 | Aug. 19, 1997 | Histamine antagonist, an interleukin-1 antagonist and/or a TNF alpha antagonist in a cosmetic, pharmaceutical or dermatological composition and composition obtained | The invention relates to the use of a histamine antagonist, an interleukin-1 antagonist and/or a TNF alpha anlagonist in a cosmetic, pharmaceutical or dermatological composition for treating sensitive skins. It relates especially to the use of a histamine antagonist, an interleukin-1 antagonist and/or a TNF alpha antagonist for preventing and/or combating skin irritations and/or sores and/or erylhema and/or dysaesthetic sensations and/or sensations of inflammation and/or pruritus and/or prickling and/or tingling and/or discomfort and/or tightness of the skin and/or mucosae. It also relates to a composition containing a histamine antagonist, an interleukin-1 antagonist and/or a TNF alpha antagonist which limits or eliminates the irritant side-effects of certain products, and in particular of certain cosmetic, dermatological or pharmaceutical active agents. |
| 5,656,644 | Aug. 12, 1997 | Pyridyl imidazoles | Novel 2,4,5-triaryl imidazole compounds and compositions for use in therapy. |
| 5,656,272 | Aug. 12, 1997 | Methods of treating TNF-alpha -mediated Crohn's disease using chimeric anti-TNF antibodies | Anti-TNF antibodies, fragments and regions thereof which are specific for human tumor necrosis factor- alpha (TNF alpha) and are useful in vivo for diagnosis and therapy of a number of TNF alpha -mediated pathologies and conditions, including Crohn's disease, as well as polynucleotides coding for murine and chimeric antibodies, methods of producing the antibody, methods of use of the anti-TNF antibody, or fragment, region or derivative thereof, in immunoassays and immunotherapeutic approaches are provided. |
| 5,654,407 | Aug. 5, 1997 | Human anti-TNF antibodies | Human monoclonal antibodies (mAbs) which bind to human TNF alpha are disclosed Autoantibodies of both the IgM and IgG isotypes are disclosed. A preferred human monoclonal antibody is known as BS (F78-1A10-B5 mAb) and it binds to recombinant human TNF alpha (rhTNF alpha) in ELISA format with a titer comparable to three high affinity neutralizing mouse mAbs. It also binds to cell surface TNF alpha and prevents TNF alpha secretion by human monocyle cell lines. |
| 5,654,323 | Aug. 5, 1997 | Heterocyclic compounds | A compound of formula (I): [See Original Patent for Chemical Structure Diagram] (I) in which X, n, B and Y are as defined in the description useful as cytokine inhibitors. |
| 5,654,312 | Aug 5, 1997 | Treatment of inflammatory and/or autoimmune dermatoses with thalidomide alone or in combination with other agents | Methods of treatment for inflammatory and autoimmune dermatoses which comprises topical and/or systemic administration of a therapeutically-effective amount of thalidomide alone or in combination with other dermatological agents. |
| 5,652,353 | Jul. 29, 1997 | DNAs encoding tumor necrosis factor- alpha muteins | It is an object of this invention to provide a human Tumor Necrosis Factor mutein or a pharmaceutically acceptable salt thereof characterized in that the TNF sequence is changed by a deletion, insertion, substitution or combinations thereof, of one or more amino acids so that the mutein shows a significant difference between its binding affinity to the human p75-Tumor-Necrosis-Factor-Receptor and to the human p55-Tumor-Necrosis-Factor-Receptor. The invention also includes DNA sequences coding for such muteins, vectors comprising such DNA sequences, host cells transformed with such vectors and a process for the production of such muteins employing such transformed host cells and pharmaceutical compositions containing such muteins and theiruse for the treatment of illnesses, for example cancer. |
| 5,652,243 | Jul. 29, 1997 | Methods of using enantiomerically pure hydroxylated xanthine compounds | There is disclosed compounds and pharmaceutical compositions that are a resolved R or S (preferably R) enantiomer of an omega -1 alcohol of a straight chain alkyl (C5–8) substituted at the 1-position of 3,7-disubstituted xanthine. The inventive compounds are effective in modulating cellular response to external or in situ primary stimuli, as well as to specific modes of administration of such compounds in effective amounts. |
| 5,650,396 | Jul. 22, 1997 | Methods of modulating inflammatory cytokines in the CNS using TGF- beta | Methods for modulating the expression of inflammatory cytokines in the central nervous system comprising administering an effective amount of TGF- beta are disclosed. The methods include suppressing pro-inflammatory cytokines in the central nervous system by administering an effective amount of TGF- beta and inducing anti-inflammatory cytokines in d the central nervous system by administering an effective amount of TGF- beta. |
| 5,650,316 | Jul. 22, 1997 | Uses of triplex forming oligonucleotides for the treatment of human diseases | The present invention provides novel methods of treating anti-neopastic and non-neoplastic cell proliferative diseases. The present methods involve administration of triplex forming oligonucleotides to humans to inhibit the biological activity of tumor necrosis factor. Also provided are methods of treating neuro-oncologic states and renal cancer. |

TABLE 2-continued

Exemplary Anti-Cytokine Compounds

| Patent No. | Issue Date | Title | Abstract |
|---|---|---|---|
| 5,648,359 | Jul. 15, 1997 | Tumor necrosis factor production inhibitors | There is provided a composition for inhibiting the production or secretion of tumor necrosis factor effective for the treatment of cachexia, septic shock, multiple organ failure, rheumatoid arthritis, inflammatory bowel disease, multiple sclerosis, osteoarthritis, Behcet disease, systemic lupus erythematosus (SLE), graft versus host disease (GvHD), malaria, acquired immune deficiency syndrome (AIDS), meningitis, hepatitis and Type II diabetes mellitus. The composition comprises a pharmaceutically effective amount of a compound of formula (1). |
| 5,646,158 | Jul. 8, 1997 | 1,3,3-(trisubstituted)cyclohex-1-ene monomers and related compounds | This invention relates to certain 1,3,3-(trisubstituted)cyclohex-1-ene monomers and related compounds which are useful in treating allergic and inflammatory diseases and for inhibiting the production of Tumor Necrosis Factor (TNF). |
| 5,646,154 | Jul. 8, 1997 | Pharmaceutical compositions for inhibiting the formation of tumor necrosis factor | Quinazoline compounds represented by general formula (1) or (2) possess an activity of significantly inhibiting the production or secretion of a tumor necrosis factor and are useful as drugs for the treatment of diseases wherein a tumor necrosis factor is considered to be involved in causing those diseases: [See Original Patent for Chemical Structure Diagram] (1) [See Original Patent for Chemical Structure Diagram] (2) wherein R<1> through R<7> and A represent specific functional groups. |
| 5,646,128 | Jul. 8, 1997 | Methods for treating adenosine kinase related conditions | Novel compounds which selectively inhibit adenosine kinase and methods of preparing adenosine kinase inhibitors are provided. Also provided are methods of treating various inflammatory conditions, including arthritis and SIRS, which may be ameliorated by increased ocal concentrations of adenosine using adenosine kinase inhibitors. |
| 5,644,034 | Jul. 1, 1997 | Tumour necrosis factor binding ligands | The present invention relates to ligands which bind to human tumour necrosis factor alpha (TNF) in a manner such that upon binding of these ligands to TNF the biological activity of TNF is modified. In preferred forms the ligand binds to TNF in a manner such that the induction of endothelial procoagulant activity of the TNF is inhibited; the binding of TNF to receptors on endothelial cells is inhibited; the induction of fibrin deposition in the tumor and tumor regression activities of the TNF are enhanced; and the cytotoxicity and receptor binding activities of the TNF are unaffected or enhanced on tumor cells. The ligand is preferably an antibody, F(ab) fragment, single domain antibody (dABs) single chain antibody or a serum binding protein. It is preferred, however, that the ligand is a monoclonal antibody or F(ab) fragment thereof. |
| 5,643,946 | Jul. 1, 1997 | Compounds useful for treating allergic and inflammatory diseases | Compounds of the formula [See Original Patent for Chemical Structure Diagram] wherein the substituents are as defined herein, are disclosed. Pharmaceutical compositions and methods of treating allergic and inflammatory diseases are also taught. |
| 5,643,915 | Jul. 1, 1997 | Treatment of ischemia/reperfusion injury with thalidomide alone or in combination with other therapies | In accordance with the present invention, a method is provided for treating reperfusion injury, ischemia and runaway inflammatory conditions with thalidomide alone or in combination with other drugs selected from the group consisting of nitrates, beta-adrenoceptor blocking agents, anti-platelet/thrombolytic drugs, drugs acting as the arachindonic acid cascade and calcium antagonists. Pharmaceutical compositions comprising thalidomide alone or in combination with other drugs are also provided. |
| 5 643,893 | Jul. 1, 1997 | N-substituted-(Dihydroxyboryl)alkyl purine, indole and pyrimidine derivatives, useful as inhibitors of inflammatory cytokines | Novel N-substituted-(dihydroxyboryl)alkyl purine, indole and pyrimidine derivatives have been found to be useful as inhibitors of inflammatory cytokines. They can be used inter alia, in the therapy of septic shock, cachexia, rheumatoid arthritis, inflammatory bowel disease, multiple sclerosis and AIDS. The compounds are typically prepared by reaction of an bromoalkyl boronic acid with the purine, indole or pyrimidine base. |
| 5,643,570 | Jul. 1, 1997 | BPI-immunoglobulin fusion proteins | Disclosed are novel hybrid fusion proteins comprising at their amino terminus, bactericidal/permeability-increasing protein or a biologically active fragment thereof and, at their carboxy terminus, at least one immunoglobulin heavy chain constant domain useful in treating bacterial infection. Also disclosed are DNA sequences encoding such proteins, recombinant methods for production of the proteins, and pharmaceutical preparations containing the recombinant products. |
| 5,641,783 | Jun. 24, 1997 | Substituted amino alcohol compounds | Disclosed are compounds having a straight or branched aliphatic hydrocarbon structure of formula [See Original Patent for Chemical Structure Diagram] I In formula I, n is an integer from one to four and m is an integer from four to twenty. Independently, R1 and R2 are hydrogen, a straight or branched chain alkyl, alkenyl or alkynyl of up to twenty carbon atoms in length or —(CH2)[w]R5. If R1 or R2 is —(CH2)[w]R5, w may be an integer from one to twenty and R5 may be an hydroxyl, halo, C1–8 alkoxyl group or a substituted or unsubstituted carbocycle or heterocycle. Alternatively, R1 and R2 may jointly form a substituted or unsubstituted, saturated or unsaturated heterocycle having from four to eight carbon atoms, N being a hetero atom of the resulting heterocycle. R3 may be either hydrogen or C1–3. In the compounds, a total sum of carbon atoms comprising R1 or R2, (CH2)[n] and (CH2)[m] does not exceed forty. R4 is a terminal moiety comprising a substituted or unsubstituted, oxidized or reduced ring system, the ring system having a single ring or two to three fused rings, a ring comprising from three to seven ring atoms. The disclosed compounds are effective agents to inhibit undesirable responses to cell stimuli. |
| 5,641,751 | Jun. 24, 1997 | Tumor necrosis factor inhibitors | Peptides which consist of 4–25 amino acids and which bind to tumor necrosis factor-alpha, prevent tumor necrosis factor-alpha from binding to its receptors and inhibit tumor necrosis factor-alpha activity are disclosed. Methods of inhibiting tumor necrosis factor-alpha activity and of treating individuals suffering from tumor necrosis factor-alpha-mediated diseases and disorders are disclosed. |

TABLE 2-continued

Exemplary Anti-Cytokine Compounds

| Patent No. | Issue Date | Title | Abstract |
|---|---|---|---|
| 5,639,597 | Jun. 17, 1997 | Cell-free receptor binding assays, the production and use thereof | The invention reates to cell-free receptor binding assays which permit the binding behavior of receptor proteins in the cell membrane toward natural or artificial ligands to be investigated. This entails the particular receptor being linked to a suitable carrier molecule, preferably the heavy chain of an immunoglobulin, and being bound via the carrier, with retention of its biological property, to a suitable solid phase. |
| 5,639,593 | Jun. 17, 1997 | Method for determining TNF | Compositions and methods are described for identifying inhibitors of mature protein hormone formation from a prohormone, and prophylactic and therapeutic uses of the inhibitors for treating diseases associated with elevated levels of the mature hormones, particulary sepsis, AIDS and autoimmune diseases. |
| 5,635,517 | Jun. 3, 1997 | Method of reducing TNF alpha levels with amino substituted 2-(2,6-dioxopiperidin-3-yl)-1-oxo- and 1,3-dioxoisoindolines | 1-Oxo- and 1,3-dioxo-2-(2,6-dioxopiperidin-3-yl) isoindolines substituted with amino in the benzo ring reduce the levels of TNF alpha in a mammal. A typical embodiment is 1,3-dioxo-2-(2,6-dioxopiperidin-3-yl)-5-aminoisoindoline. |
| 5,633,145 | May 27, 1997 | TNF alpha receptor-derived binding protein | A polypeptide is provided which is capable of binding human TNF alpha and which has the first three cysteine-rich subdomains, but not the fourth cysteine-rich subdomain, of the extracellular binding domain of a receptor selected from the group consisting of the 55 kD and 75 kD receptors for human TNF alpha. The ability of the polypeptide to bind TNF alpha means that it can be used for treating diseases mediated by TNF alpha activity, such as rheumatoid arthritis. |
| 5,632,982 | May 27, 1997 | Cytotoxic enhancement of TNF with copper | Copper chelates serve as cytotoxic agents in conjunction with a surface membrane protein receptor internalizing agent, particularly TNF, which has independent cytotoxic activity, for use against target cells. By employing concentrations of the two agents, where the agents have substantially reduced adverse side effects, the combination is shown to have effective cytotoxic activity. |
| 5,631,286 | May 20, 1997 | Compounds useful for treating allergic or inflammatory diseases | Novel cyclohexanes of formulas (I) and (II) are described herein. They inhibit the production of Tumor Necrosis Factor and are useful in the treatment of disease states mediated or exacerbated by TNF production: these compounds are also useful in the mediation or inhibition of enzymatic or catalytic activity of phosphodiesterase IV. [See Original Patent for Chemical Structure Diagram] (I) [See Original Patent for Chemical Structure Diagram] (II) |
| 5,631,258 | May 20, 1997 | Method of effecting immunosuppression by administering carbocyclic adenosine analogs | This invention relates to methods of effecting immunosuppression and inhibiting tumor necrosis factor alpha in a patient in need thereof comprising administering to said patient an effective immunosuppressive amount of a compound of the formula [See Original Patent for Chemical Structure Diagram] wherein the hydroxy substituent on the cydopentanyl ring is in the CIS configuration relative to the bicyclic substituent, Y3 is N, Y7, Y8 and Y9 are each independently nitrogen or a CH group, Q is NH2, halogen or hydrogen, and Z is hydrogen, halogen, or NH2; or a pharmaceutically-acceptable salt thereof. Also presented are pharmaceutical compositions comprising compounds of the same formula. |
| 5,629,315 | May 13, 1997 | Treatment of diseases using enantiomerically pure hydroxylated xanthine compounds | There is disclosed compounds and pharmaceutical compositions that are a resolved R or S (preferably R) enantiomer of an omega -1 alcohol of a straight chain alkyl (C5–8) substituted at the 1-position of 3,7-disubstituted xanthine. The inventive compounds are effective in modulating cellular response to external or in situ primary stimuli, as well as to specific modes of administration of such compounds in effective amounts. |
| 5,629,285 | May 13, 1997 | Inhibitors of TNF- alpha secretion | Compounds and methods are disclosed that are useful in inhibiting the TNF- alpha converting enzyme (TACE) responsible for cleavage of TNF- alpha precursor to provide biologically active TNF- alpha. The compounds employed in the invention are peptidyl derivatives having active groups capable of inhibiting TACE such as, hydroxamates, thiols, phosphoryls and carboxyls. |
| 5,627,262 | May 6, 1997 | Method and composition for the treatment of septic shock | The present invention contemplates a composition and method for treating septic shock in a mammal or as a prophylactic treatment prior to a surgical procedure, comprising administering a therapeutically effective amount of a bacterial lipopolysaccharide binding peptide derived from CAP37 protein. In a preferred version, the composition and method of use may comprise a peptide comprising amino acids 20–44 or 120–146 of CAP37 or subunits thereof. |
| 5,625,085 | Apr. 29, 1997 | Esters of acyl L-carnitines and pharmaceutical compositons containing same for treating endotoxic shock | Esters of alkanoyl L-carnilines wherein the alkanoyl is a saturated or unsaturated, straight or branched alkanoyl having 2-26 carbon atoms, optionally omega -substituted with trialkylammonium, dialkylsulfonium, hydroxyl, carboxyl, halogen, methanesulfonyl and hydroxysulfonyl, are useful for preparing pharmaceutical compositions for the treatment of endotoxic shock. |
| 5,624,913 | Apr. 29, 1997 | Method reducing TNF-alpha in mammals with cerebral malaria | A method for reducing the TNF-alpha in mammals with cerebral malaria comprising the administration of 2-methylthio-ATP or 2-chloro-ATP. |
| 5,616,490 | Apr. 1, 1997 | Ribozymes targeted to TNF- alpha RNA | An enzymatic RNA molecule which cleaves mRNA associated with development or maintenance of an inflammatory disease. |
| 5,614,540 | Mar. 25, 1997 | Compounds useful for treating allergic and inflammatory diseases | Novel compounds of Formula (I) [See Original Patent for Chemical Structure Diagram] where X4 is a substituted cyclohexane or cyclohexane group and the other radicals are defined herein. These compounds inhibit the production of Tumor Necrosis Factor and are useful in the treatment of disease states mediated or exacerbated by TNF production. The compounds of the present invention are also useful in the mediation or inhibition of enzymatic or catalyyic activity of phosphodiesterase IV and are therefore useful in the treatment of disease states in need of mediation or inhibition thereof. |

TABLE 2-continued

Exemplary Anti-Cytokine Compounds

| Patent No. | Issue Date | Title | Abstract |
|---|---|---|---|
| 5,612,476 | Mar. 18, 1997 | Anti-endotoxin compounds | Disclosed are lipid A analogs useful for the treatment of septic shock and LPS-mediated activation of viral infection. |
| 5,612,349 | Mar. 18, 1997 | Enantiomerically pure hydroxylated xanthine compounds to treat shock symptoms | There is disclosed compounds and pharmaceutical compositions that are a resolved R or S (preferably R) enantiomer of an omega -1alcohol of a straight chain alkyl (C[5–8]) substituted at the 1-position of 3,7-disubstituted xanthine. The inventive compounds are effective in modulating cellular response to external or in situ primary stimuli, as well as to specific modes of administration of such compounds in effective amounts. |
| 5,610,279 | Mar. 11, 1997 | Human TNF receptor | The present invention is concerned with non-soluble proteins and soluble or insoluble fragments thereof, which bind TNF, in homogeneous form, as well as their physiologically compatible salts, especially those proteins having a molecular weight of about 55 or 75 kD (non-reducing SDS-PAGE conditions), a process for the isolation of such proteins, antibodies against such proteins, DNA sequences which code for non-soluble proteins and soluble or non-soluble fragments thereof, which bind TNF, as well as those which code for proteins comprising partly of a soluble fragment, which binds TNF, and partly of all domains except the first of the constant region of the heavy chain of human immunoglobulins and the recombinant proteins coded thereby as well as a process for their manufacture using transformed pro- and eukaryotic host cells. |
| 5,606,023 | Feb. 25, 1997 | Mutant tumor necrosis factor proteins | Mutant tumor necrosis factor proteins which retain full or near full capability to bind to a TNFR-p75 receptor while retaining only a limited capability to bind a TNFR-p55 receptor are provided. Methods of inhibiting toxicity induced by tumor necrosis factor by treating cells or tissues having a tumor necrosis factor receptor with these mutant human tumor necrosis factor proteins are also provided. Pharmaceutical compositions and methods of inhibiting systemic tumor necrosis factor induced toxicity in a p atient undergoing antitumor TNF- alpha therapy with these compositions are also provided. |
| 5,605,923 | Feb. 25, 1997 | Compounds useful for treating inflammatory diseases and inhibiting production of tumor necrosis factor | Novel cyclohexene-ylidene derivatives of formula (I) are described herein. These compounds inhibit the production of Tumor Necrosis Factor and are useful in the treatment of disease states mediated or exacerbated by TNF production; they are also useful in the mediation or inhibition of enzymatic or catalylic activity of phosphodiesterase IV and are therefore useful in the treatment of disease states in need of mediation or inhibition thereof. [See Original Patent for Chemical Structure Diagram] (I) |
| 5,605,914 | Feb. 25, 1997 | Imides | Cyclic imides are inhibitors of tumor necrosis factor alpha and can be used to combat cachexia, endotoxic shock, and retrovirus replication. A typical embodiment is 2-(2,6-dioxo-3-piperidinyl)-4-azalsoindoline-1,3-dione. |
| 5,605,826 | Feb. 25, 1997 | 24 kilodalton cyloplasmic protease activating DNA fragmentation in apoptosis | An apoptosis-associated protease having a relative mass of 24 kilodaltons and a defined amino acid composition is disclosed, togetherwith a method for its purification from a cyloplasmic extract of mammalian cells treated with an apoptosis-inducing agent, such as tumor necrosis factor- alpha or UV irradiation, that comprises affinity chromatography with the serine protease inhibitor DK120 followed by heparin-sepharose chromatography. The protease has activity against the elastase-like substrate MAAPV and is capable of inducing apoptosis in isolated U937 cell target nuclei. |
| 5,605,690 | Feb. 25, 1997 | Methods of lowering active TNF- alpha levels in mammals using tumor necrosis factor receptor | A method for treating TNF-dependent inflammatory diseases in a mammal by administering a TNF antagonist, such as soluble TNFR. |
| 5,602,173 | Feb. 11, 1997 | Compounds useful for treating allergic and inflammatory diseases | Novel cyclohexane-ylidene derivatives of formula (I) are described. These compounds inhibit the production of Tumor Necrosis Factor and are useful in the treatment of disease states mediated or exacerbated by TNF production. These compounds are also useful in the mediation or inhibition of enzymatic or catalylic activity of phosphodiesterase IV and are therefore useful in the treatment of disease states in need of mediation or inhibition thereof. [See Original Patent for Chemical Structure Diagram] (I) |
| 5,602,166 | Feb. 11, 1997 | Cytokine inhibitors | Invented are methods of inhibiting the production of cytokines, particularly inhibiting the production of interleukin-1 and inhibiting the production of tumor necrosis factor in a mammal in need thereof which comprises administering to such mammal an effective amount of an azaspirane derivative. |
| 5,602,157 | Feb. 11, 1997 | Compounds useful for treating allergic and inflammatory diseases | Novel compounds or formula (I) are described herein. These compounds inhibit the production of Tumor Necrosis Factor and are useful in the treatment of disease states mediated or exacerbated by TNF production. The compounds or present invention are also useful in the mediation or inhibition of enzymatic or catalytic activity of phosphodiesterase IV and are therefore useful in the treatment of disease states in need of mediation or inhibition therefore. [See Original Patent for Chemical Structure Diagram] (I) |
| 5,597,899 | Jan. 28, 1997 | Tumor necrosis factor muteins | Human TNF muteins having higher binding affinity for human p75-TNF receptor than for human p55-TNF receptor indude muteins having at least one different amino acid relative to wild-type human TNF at a position corresponding to position 33, 65, 67, 75, 87, 143, 145 or 147 of the wild-type amino acid sequence. |
| 5,594,106 | Jan. 14, 1997 | Inhibitors of TNF- alpha secretion | Compounds and methods are disclosed that are useful in inhibiting the TNF- alpha converting enzyme (TACE) responsible for cleavage of TNF- alpha precursor to provide biologically active TNF- alpha. The compounds employed in the invention are peptidyl derivatives having active groups capable of inhibiting TACE such as, hydroxamates, thiols, phosphoryls and carboxyls. |
| 5,593,992 | Jan. 14, 1997 | Compounds | Novel 1,4,5-substituted imidazole compounds and compositions for use in therapy as cytokine inhibitors. |
| 5,593,991 | Jan. 14, 1997 | Imidazole compounds, use and process of making | Novel 1,4,5-substituted imidazole compounds and compositions for use in therapy as cytokine inhibitors. |

Throughout the present specification, reference has been made to various patent and non-patent publications, including the patents listed in Table 2. The entire disclosure of each such reference is incorporated herein by reference. The disclosure of U.S. patent application Ser. No. 60/084,668, filed on May 7, 1998, is also incorporated herein by reference.

Although the invention has been described with reference to the presently preferred embodiment, it should be understood that various modifications will become apparent to those of skill in the art upon review of the present disclosure. Such modifications are intended to be within the scope of the present invention.

We claim:

1. A method for diagnosing chronic pelvic pain syndrome or non-bacterial prostatitis in a subject experiencing chronic, episodic pain in the perineum or pelvic region. irritative and obstructive voiding symptoms and/or adverse effects on sexual function, said method comprising determining the level of one or more cytokines in semen from the subject, or in a component or fraction of such semen, wherein the one or more cytokines comprise a first group of one or more cytokines selected from the group consisting of GM-CSF and IL-8, whereby an elevated level of one or more of the cytokines indicates the presence of chronic pelvic pain syndrome or non-bacterial prostatitis.

2. The method of claim 1 wherein the condition is non-bacterial prostatitis.

3. The method of claim 1 wherein the condition is chronic pelvic pain syndrome.

4. The method of claim 1 wherein the level of the one or more cytokines is measured in seminal fluid or a fraction or component thereof.

5. The method of claim 1 wherein the level of the one or more cytokines is measured in seminal plasma.

6. The method of claim 1 wherein the cytokine level is measured by an immunoassay.

7. The method of claim 1 wherein the one or more cytokines further comprise a second group of one or more cytokines selected from the group consisting of IL-1-$\beta$, Il-6, and TNF-$\alpha$.

8. The method of claim 7 wherein the second group of one or more cytokines comprises TNF-$\alpha$.

9. The method of claim 7 wherein the second group of one or more cytokines comprises IL-1$\beta$.

10. The method of claim 7 wherein the second group of one or more cytokines comprises IL-6.

11. The method of claim 1 wherein the first group of one or more cytokines comprises GM-CSF.

12. The method of claim 1 wherein the first group of one or more cytokines comprises IL-8.

13. A method for diagnosing chronic pelvic pain syndrome in a subject, said method:

(a) comprising determining the level of GM-CSF and/or IL-8 in semen from the subject, or a component or fraction of such semen, whereby the presence of GM-CSF and/or IL-8 in the semen or in the component or fraction of the semen indicates chronic pelvic pain syndrome; and (b) optionally comprising determining the level of IL-1$\beta$Il-6 and/or TNF-$\alpha$ in semen from the subject, or a component or fraction of such semen, whereby the presence of IL-1$\beta$, Il-6 and/or TNF-$\alpha$ in the semen or in the component or fraction of the semen is a confirmatory indicator of chronic pelvic pain syndrome.

14. A method for diagnosing a condition in a subject, wherein said condition is associated with elevated levels of GM-CSF, said method comprising determining the level of GM-CSF in semen from the subject, or in a component or fraction of such semen.

* * * * *

UNITED STATES PATENT AND TRADEMARK OFFICE
CERTIFICATE OF CORRECTION

PATENT NO. : 6,180,355 B1
DATED : January 30, 2001
INVENTOR(S) : Richard B. Alexander, Sathibalan Ponniah It is certified that error appears in the above-identified patent and that said Letters Patent is hereby corrected as shown below:

Column 4,
Line 62, change "type 11" to -- type II --

Column 11,
Line 51, change "β1" to -- µ1 --.
Line 57, change "HCI" to -- HCI --.

Column 16,
Line 39, change "2,6-dioxo-34luoropiperidin-3-yl-isoindoline" to
-- 2,6-dioxo-3-fluoropiperidin-3-yl)-isoindoline --.

Column 18,
Line 28, change "cottagenase" to -- collagenase --.

Column 20,
Line 4, change "cyloplasmic" to -- cytoplasmic --.

Column 22,
Line 35, change "cylotoxic" to -- cytotoxic --.
Line 42, change "Disdosed" to -- Disclosed --.

UNITED STATES PATENT AND TRADEMARK OFFICE
CERTIFICATE OF CORRECTION

PATENT NO. : 6,180,355 B1
DATED : January 30, 2001
INVENTOR(S) : Richard B. Alexander, Sathibalan Ponniah It is certified that error appears in the above-identified patent and that said Letters Patent is hereby corrected as shown below:

Column 23,
Line 6, change "pharmaceutica(" to -- pharmaceutical --.

Column 26,
Line 44, change "asspcoatopm" to -- association --.
Line 58, change "VCAM-1isprovided" to -- VCAM-1 is provided --.

Column 29,
Line 36 "her2" to -- HER2 --.

Column 30,
Line 4, change "cylotoxic" to -- cytotoxic --.
Line 36, change "celts" to -- cells --.
Line 55, change "tymphokine" to -- lymphokine --.
Line 60, change "hetminth" to -- helminth --.

Column 32,
Line 20, change "retease" to -- release --.
Line 73, change "wetI" to -- well --.

Column 34,
Line 4, change "independentty" to -- independently --.
Line 8, change "interteukin" to -- interleukin --.
Line 9, change "granutocyte" to -- granulocyte --.
Line 47, change "Phospoiipid" to -- Phospholipid --.

Column 36,
Line 73, change "1tumor" to -- 1 tumor --.
Line 73, change "G1and" to -- G1 and --.

Column 37,
Line 2, change "imideslamides" to -- imides/amides --.

Column 38,
Line 31, change "gto" to -- to --.

UNITED STATES PATENT AND TRADEMARK OFFICE
CERTIFICATE OF CORRECTION

PATENT NO. : 6,180,355 B1
DATED : January 30, 2001
INVENTOR(S) : Richard B. Alexander, Sathibalan Ponniah It is certified that error appears in the above-identified patent and that said Letters Patent is hereby corrected as shown below:

Column 39,
Line 63, change "cartiiage" to -- cartilage --.

Column 40,
Line 17, change "these" to -- these --.
Line 19, change "Formula [See" to -- Formula 1: [See --.
Line 43, change "Thymocyle" to -- Thymocyte --.
Line 44, change "lymphocyle" to -- lymphocyte --.
Line 50, change "piay" to -- play --.
Line 52, change "vanous" to -- various --.
Line 57, change "nucieoside" to -- nucleoside --.

Column 41,
Line 46, change "transcnpts" to -- transcripts --.

Column 42,
Line 14, change "disdosed" to -- disclosed --.
Line 30, change "lymphocyle" to -- lymphocyte --.
Line 40, change "lymphocyle" to -- lymphocyte --.
Line 53, change "bocly" to -- body --.
Line 56, change "nordihydrogualaretic" to -- nordihydroguaiaretic --.
Line 69, change "disdosed" to -- disclosed --.

Column 44,
Line 22, change "erylhema" to -- erythema --.
Line 38, change "BS" to -- B5 --.
Line 41, change "monocyle" to -- monocyte --.
Line 57, change "theiruse" to -- their use --.
Line 67, change "in d" to -- in --.

Column 46,
Line 21, change "ocal" to -- local --.
Line 54, change "formula [" to -- formula I: [--

Column 48,
Line 58, change "L-carnilines" to -- L-carnitines --.

UNITED STATES PATENT AND TRADEMARK OFFICE
CERTIFICATE OF CORRECTION

PATENT NO. : 6,180,355 B1
DATED : January 30, 2001
INVENTOR(S) : Richard B. Alexander, Sathibalan Ponniah It is certified that error appears in the above-identified patent and that said Letters Patent is hereby corrected as shown below:

Column 49,
Line 34, change "cyloplasmic" to -- cytoplasmic --.

Column 50,
Line 9, change "welI" to -- well --.
Line 13, change "soiuble" to -- soluble --.
Line 23, change "p atient" to -- patient --.
Line 33, change "azalsoindoline" to -- azaisoindoline --.
Line 36, change "cyloplasmic" to -- cytoplasmic --.
Line 62, change "indude" to -- include --.

Column 52,
Line 25, change "IL-1βI1-6" to -- IL-1β, I1-6 --.

Signed and Sealed this

Thirtieth Day of October, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO.    : 6,180,355 B1
DATED         : January 30, 2001
INVENTOR(S)   : Richard B. Alexander and Sathibalan Ponniah It is certified that error appears in the above-identified patent and that said Letters Patent is hereby corrected as shown below:

Column 1,
Line 4, between the title and "CROSS-REFERENCE TO RELATED APPLICATION," insert the following text:

--           GOVERNMENT RIGHTS IN INVENTION
Work related to the invention was done in the performance of NIH Grant No. DK53732-03 funded by the United States National Institutes of Health. The government has certain rights in the invention. --

Signed and Sealed this

Fourteenth Day of January, 2003

JAMES E. ROGAN
*Director of the United States Patent and Trademark Office*